(12) United States Patent
Callas

(10) Patent No.: US 7,979,289 B2
(45) Date of Patent: Jul. 12, 2011

(54) SYSTEM AND METHOD FOR INTELLIGENT MANAGEMENT OF MEDICAL CARE

(75) Inventor: Constantine Callas, Santa Ana, CA (US)

(73) Assignee: The Callas Group, LLC, Santa Ana, CA (US)

( * ) Notice: Subject to any disclaimer, the term of this patent is extended or adjusted under 35 U.S.C. 154(b) by 0 days.

(21) Appl. No.: 12/197,063

(22) Filed: Aug. 22, 2008

(65) Prior Publication Data
US 2009/0210251 A1    Aug. 20, 2009

Related U.S. Application Data

(60) Provisional application No. 60/968,032, filed on Aug. 24, 2007.

(51) Int. Cl.
*G06F 19/00* (2006.01)

(52) U.S. Cl. .......................................... 705/3

(58) Field of Classification Search ................ 705/2, 4; 364/401
See application file for complete search history.

(56) References Cited

U.S. PATENT DOCUMENTS

| | | | |
|---|---|---|---|
| 5,253,164 A | 10/1993 | Holloway et al. | |
| 5,359,509 A | 10/1994 | Little et al. | |
| 5,519,607 A | 5/1996 | Tawil | |
| 5,557,514 A * | 9/1996 | Seare et al. | 705/2 |
| 5,778,345 A * | 7/1998 | McCartney | 705/2 |
| 5,924,073 A | 7/1999 | Tyuluman et al. | |
| 5,933,809 A | 8/1999 | Hunt et al. | |
| 6,826,536 B1 | 11/2004 | Forman | |
| 6,879,959 B1 * | 4/2005 | Chapman et al. | 705/2 |
| 7,194,416 B1 | 3/2007 | Provost et al. | |
| 7,222,079 B1 | 5/2007 | Seare et al. | |
| 7,263,492 B1 | 8/2007 | Suresh et al. | |
| 7,356,460 B1 | 4/2008 | Kennedy et al. | |
| 2002/0019754 A1 | 2/2002 | Peterson et al. | |
| 2002/0095313 A1 * | 7/2002 | Haq | 705/2 |
| 2003/0135397 A1 | 7/2003 | Halow et al. | |
| 2003/0149597 A1 * | 8/2003 | Zaleski | 705/2 |
| 2004/0010136 A1 * | 1/2004 | Au-Young et al. | 536/24.3 |
| 2006/0259324 A1 * | 11/2006 | Patterson | 705/2 |
| 2006/0287879 A1 | 12/2006 | Malone | |
| 2007/0250352 A1 | 10/2007 | Tawil | |

OTHER PUBLICATIONS

"Superficial Heat and Cold: How to Maximise the Benefits", Anderson, Owen, The Physician and Sportsmedicine, vol. 22 (12), pp. 65-74, 1994).*
HCFA 1500 Health Claim Form.*

* cited by examiner

*Primary Examiner* — Gerald J. O'Connor
*Assistant Examiner* — John A Pauls
(74) *Attorney, Agent, or Firm* — Christie, Parker & Hale, LLP

(57) ABSTRACT

A computerized medical care system provides validation of a diagnosis of a medical condition and requested medical services for treating the medical condition. The medial care system invokes multiple filters to determine the appropriateness of the diagnosis and medical service. Real time feedback is provided based on the determination. If the medical care cannot be validated, the feedback includes the reasons for the failure to validate, and any supporting materials for the lack of validation. The feedback may also prompt the requesting entity to provide additional information to help support the medical provider's position as to why the requested medical care is appropriate.

77 Claims, 31 Drawing Sheets

FIG. 8

Screen 7: The Data Entry Screen for the First Treatment or Diagnostic Procedure

Screen 8: The Data Entry Screen for the Second Treatment or Diagnostic Procedure

| | |
|---|---|
| Date: | 7/5/2007 |
| To: | BRAIN M.D., JOSIAH<br>427 COUNTRY CLUB RD SUITE 11A<br>MORGANTOWN, WV 26505<br><br>email: josiahbrainmd@provider.com |
| From: | John R. Jones, M.D.<br>Medical Director<br>Reliable Insurance Company<br>123 North Reliable Road<br>Los Angeles, CA 92770-1320<br>(310)-123-4567 ext 2000 |
| Claimant: | GARTH RIDGEFIELD |
| Claim Number: | 924858973524 |
| DOI: | 5/05/2004 |
| Request Num.: | 2007070517336 |

Subject: Authorization of Treatment Plan

On 7/5/2007 you requested authorization for a treatment plan for your patient named GARTH RIDGEFIELD. You are treating the patient for the following conditions:

| ICD-9 | ICD-9 Description |
|---|---|
| 847.0 | NECK SPRAIN |
| 722.52 | DEGENERATION LUMBAR LUMBOSACRAL DISC |

On 7/5/2007 you submitted a request to perform the following procedures for treatment of the above captioned patient:

| CPT Code | CPT Description |
|---|---|
| 63030 | SURGERY NERVOUS SYSTEM SPINE AND SPINAL CORD LAMINOTOMY WITH DECOMPRESSION OF NERVE ROOTS INCLUDING PARTIAL FACETECTOMY FORAMINOTOMY AND OR EXCISION OF HERNIATED INTERVERTEBRAL DISK ONE INTERSPACE LUM |

FIG. 11A

RELIABLE
INSURANCE

Claimant Name :    GARTH RIDGEFIELD
Claim Number :    924858973524
Provider Name :    BRAIN M.D., JOSIAH
Request Number :    2007070517336

| CPT Code | CPT Description |
|---|---|
| 99203 | EVALUATION AND MANAGEMENT OFFICE OR OUTPATIENT VISIT NEW PATIENT WITH DETAILED PROBLEM FOCUSED HISTORY EXAMINATION MEDICAL DECISION MAKING OF LOW COMPLEXITY 30 MINUTES |

In your request you indicated that you were charging the following amount for the procedures:

| Code | Mod1 | Mod2 | Date | Charge |
|---|---|---|---|---|
| 63030 | 00 | 00 | 07/06/2007 | 5000.00 |
| 99203 | 00 | 00 | 07/06/2007 | 200.00 |

Attached please find the following documents:

1. Analysis of Proposed Charges

Some of these documents do request some additional information. Please respond as soon as possible because we do want to serve the needs of this patient as soon as possible.

Please submit all communication regarding the requested information to me. You may contact me, or my staff, in any of the following methods:

mail:    John R. Jones, M.D.
         Medical Director
         Reliable Insurance Company
         123 North Reliable Road
         Los Angeles, CA 92770-1320
e-mail:   medical_director@reliable_insurance_co.com
phone:   (310)-123-4567 ext 2000

John R. Jones, M.D.
Medical Director

FIG. 11B

Claimant Name :     GARTH RIDGEFIELD
Claim Number :      924858973524
Provider Name :     BRAIN M.D., JOSIAH
Request Number :    2007070517336

ANALYSIS OF PROPOSED CHARGES

Your proposed charges for procedures were compared to the allowance values found in the Official Medical Fee Schedule (OMFA) of the California Workers' Compensation Division of Industrial Injuries and established by the Administrative Director of the Division, pursuant to Section 5307.1 and Section 5307.3 of the California Labor Codes.

The Fee Schedule recommends the following allowances for the procedures proposed in your treatment plan:

| FS Service Code | Date | Allowance |
| --- | --- | --- |
| 63030 | 07/06/2007 | 994.47 |
| 99203 | 07/06/2007 | 102.37 |

Therefore, we will authorize payment for allowances consistent with the above values. However, if you could submit information which indicates that the services you are rendering are greater than those described by the descriptors of the procedures you proposed, then we would re-evaluate your request.

FIG. 11C

DATE: _____

TO: _____

FROM: _____

On <DATE>, you submitted requests for authorization to treat patient <CLAIMANT>. While submitting information for diagnoses <ICD-9> and <ICD-9>, you were asked several questions regarding those diagnoses. You were asked those specific questions in order to assist us in validating the diagnoses. The questions were framed by our medical staff who were asked to frame questions both from their accumulated experiences and from articles found in their search of world medical literature regarding those diagnoses. Your answers to those questions were not consistent with answers that we feel would validate those diagnoses. We do not dispute the possibility the patient suffers from any of those conditions, but feel that we must assure ourselves that the patient does have those conditions.

Attached to this request are several journal articles which assisted us in framing the questions you were asked.

In order to assist us in the validation process, we are requesting that you submit additional medical information which you used in making the diagnoses. Further, it would be helpful if you would submit journal articles from the medical literature, less than five years old, that support your answers to the questions. Upon receipt of the submitted information or journal articles, we will reevaluate your request.

Please submit this information as soon as possible because we do not want to withhold valuable treatment of the patient's condition. Thank you in advance for your cooperation in this matter.

SYSTEM AND METHOD FOR INTELLIGENT MANAGEMENT OF MEDICAL CARE

CROSS-REFERENCE TO RELATED APPLICATIONS

This application claims the benefit of U.S. Provisional Application No. 60/968,032, filed Aug. 24, 2007, the content of which is incorporated herein by reference.

FIELD OF THE INVENTION

The present invention is generally related to computer systems in the field of managed care, and more particularly, to a computerized medical care system for managing and delivering information to members of the medical service industry useful for providing efficient and improved services to patients.

BACKGROUND

One problem encountered by both physicians and patients in the managed care system is the delays it causes. Studies reveal that in many cases, managed care organizations delay responses to requests for medical services for more than two or three days. Physicians feel it is non-physicians managing the system who have no medical training that causes the delay. Patients feel that the system is designed to deny rather than improve services. Despite the reasons, studies reveal that the delays are too often dangerous for the patient.

In this regard, the managed care system often requires service providers to seek authorization before providing certain services for a customer. In some cases, such authorization is improperly denied, to the detriment of the customer's welfare. The denial may arise because individuals who decided to deny the authorization were not sufficiently knowledgeable and/or because the individuals did not have the proper and/or necessary information at their disposal at the time of the decision. Although historically, management of medical care and delivery of services were in the hands of physicians, more recently, the management of medical care has been relegated to persons who are not physicians. This change is mainly due to an attempt to control the increasingly excessive costs associated with those medical services.

As one example, in an industry such as the health-care industry, certain services may be denied to a patient because decision-makers do not have at their disposal information that would support a decision to grant the services. For example, medical providers may use diagnostic codes to identify certain medical conditions. Based on an erroneous diagnostic code entered by a provider, an administrator may improperly deny a patient a certain service, e.g., a magnetic resonance imaging (MRI) of the shoulder. Although a review of the patient's medical history (e.g., medical chart) would have revealed instances of arthritis which would have made an MRI appropriate, an erroneously entered diagnostic code for an instance of trauma instead of arthritis results in the denial of the MRI. As such, medical personnel attending to the patient cannot perform the MRI, which should have been performed to treat the patient's arthritis.

As another example, reimbursement for services already provided is not approved because authorization for the services was not previously granted. For example, a coma victim may be refused reimbursement for costs associated with traveling to the hospital via ambulance because authorization for this service was not granted before the service was provided.

Studies also reveal that the nurses and managed care personnel often make decisions with insufficient information, and achieve results contrary to the best interests of the patient.

Another problem with current managed care systems is the high costs associated with such systems. The average cost to insurance companies for delivery of managed care plans ranges between $50 and $150. The reason for the increased cost is because the nursing staff, who is required to make the decisions, may take from a few hours to a few days, in making such decisions.

Prior art systems and methods exist for allowing a claims processing person to detect fraudulent medical claims that are submitted for reimbursement or payment. Although such prior art systems analyze the submitted service codes during claims processing, such analysis is for ensuring that the payment for the medical services that were already provided is appropriate. The analysis is not for improving the medical services that are provided to patients, nor to allow those medical services to be provided more efficiently.

In fact, because the submitting of the claim generally means that the service has already been performed, even if a prior art system were to substitute a procedure code that is listed in a medical claim for payment with another more appropriate code, the medical provider would not be able to change the actual procedure that would already have been performed. This may be a detriment to not only a patient that could have received a more appropriate service, but also to the rendering medical provider who is only able to get reimbursed for the procedure that should have been provided, but not the service that was actually provided.

As such, there is a need for a computerized medical care system for providing service providers and service personnel with information that is useful in providing an improved and more efficient level of service to the customers that they serve.

SUMMARY OF THE INVENTION

According to one embodiment, a method for providing a medical pre-approval in a computerized medical care system includes receiving from a requesting device a medical code associated with a medical determination; identifying one or more filters enabled for the computerized medical care system; applying the identified one or more filters for the received medical code; determining validity of the medical determination based on the applied one or more filters; and providing feedback to the requesting device based on the determination of the validity of the medical determination. The feedback prompts modification of the medical determination that is ultimately rendered to a patient if the medical determination is not validated.

According to one embodiment of the invention, the medical code is a diagnosis code, the medical determination is diagnosis of a medical condition, and the one or more filters includes a medical diagnosis filter, wherein the feedback is configured to prompt modification of the diagnosis that is ultimately rendered to the patient if the diagnosis is not validated.

According to one embodiment of the invention, the applying of the medical diagnosis filter and the determining of the validity of the diagnosis includes displaying a question that should be considered in making the diagnosis of the medical condition; prompting a user response to the displayed question; receiving the user response to the displayed question; comparing an expected response to the displayed question with the received user response; and validating the diagnosis if the expected response matches the received user response.

According to one embodiment of the invention, the method includes adding to a historical database information on the validity of the diagnosis code in association with a medical provider providing the diagnosis code; calculating based on information in the historical database a ratio of collected diagnosis codes that have not been validated to collected diagnosis codes that have been validated; and generating a report based on the ratio information.

According to one embodiment of the invention, the feedback is a letter including information on the validity of the diagnosis, where the letter is generated in real time with the validating of the diagnosis.

According to one embodiment of the invention, the medical code is a service code, the medical determination is a medical service determined based on a diagnosed medical condition, and the filters include a plurality of medical procedure filters, wherein the feedback is configured to prompt modification of the medical service that is ultimately rendered to the patient if the medical service is not validated.

According to one embodiment of the invention, each of the plurality of medical procedure filters are applied one by one in sequence.

According to one embodiment of the invention, the method further includes providing a graphical user interface with a list of the plurality of medical procedure filters; receiving a user selection of desired ones of the plurality of medical procedure filters; and enabling each selected medical procedure filter for applying in making the validity determination of the determined medical service.

According to one embodiment of the invention, the applying of at least one of the plurality of medical procedure filters includes analyzing historical data collected in association with the service code from a historical database; determining based on the analyzed historical data whether the medical service is statistically reasonable; and returning a result of applying at least one of the plurality of medical procedure filters based on the determination.

According to one embodiment of the invention, the method further includes adding to the historical database information on the medical service requested for the medical condition.

According to one embodiment of the invention, at least one of the plurality of medical procedure filters is a heat filter, and the applying of the heat filter includes identifying a date of injury; identifying a timing of the medical service, wherein the medical service is a heat-based therapy; determining whether the timing of the heat-based therapy is appropriate relative to the date of injury; and returning a result of applying the heat filter based on the determination.

According to one embodiment of the invention, at least one of the plurality of medical procedure filters is a rarity filter. The applying of the rarity filter includes retrieving historical data of medical services provided for the diagnosed medical condition; identifying a rate in which the determined medical service was provided for the identified diagnosis based on the retrieved historical data; identifying a threshold rate; determining whether the identified rate satisfies the threshold rate; and returning a result of applying the rarity filter based on the determination.

According to one embodiment of the invention, at least one of the plurality of medical procedure filters is a utilization filter. The applying of the utilization filter includes receiving information on a requested number of visits or duration of care for the identified service code; analyzing historical data of previous number of visits or durations of care provided for the diagnosed medical condition; identifying a threshold number of visits or durations of care based on the analyzed historical data; determining whether the requested number of visits or duration of care satisfies the threshold number of visits or duration of care; and returning a result of applying the utilization filter based on the determination.

According to one embodiment of the invention, at least one of the plurality of medical procedure filters is a level of service filter. The applying of the level of service filter includes identifying a level of service associated with the identified service code; analyzing historical data of previous levels of service provided for the diagnosed medical condition; identifying a threshold level of service based on the analyzed historical data; determining whether the identified level of service satisfies the threshold level of service; and returning a result of applying the level of service filter based on the determination.

According to one embodiment of the invention, at least one of the plurality of medical procedure filters is a billing guidelines filter. The applying of the billing guidelines filter includes receiving a requested charge amount for the determined medical service; identifying a billing guideline associated with the determined medical service; determining whether the requested charge amount satisfies the identified billing guideline; and returning a result of applying the billing guidelines filter based on the determination.

According to one embodiment of the invention, at least one of the plurality of medical procedure filters is a charges filter. The applying of the charges filter includes receiving a requested charge amount for the determined medical service; analyzing historical data of previous charges for the diagnosed medical code; identifying a threshold charge amount based on the analyzed historical data; determining whether the identified charge amount satisfies the threshold charge amount; and returning a result of applying the charges filter based on the determination.

According to one embodiment of the invention, the feedback is a letter including information on the validity of the medical service, where the letter is generated in real time with the validating of the determined medical service.

According to one embodiment of the invention, the applying of at least one of the plurality of medical procedure filters includes identifying a specific patient for which the medical service is requested; retrieving historical data of medical care provided to the specific patient; determining based on the retrieved historical data whether the determined medical service is appropriate for the specific patient; and returning a result of applying the at least one of the plurality of medical procedure filters based on the determination.

According to another embodiment, the present invention is directed to a computerized medical care system for providing a medical pre-approval. The system includes a processor and memory operably coupled to the processor. The memory stores program instructions that are executed by the processor for receiving from a requesting device a medical code associated with a medical determination; identifying one or more filters enabled for the computerized medical care system; applying the identified one or more filters for the received medical code; determining validity of the medical determination based on the applied one or more filters; and providing feedback to the requesting device based on the determination of the validity of the medical determination, wherein the feedback prompts modification of the medical determination that is ultimately rendered to a patient if the medical determination is not validated.

According to another embodiment, the present invention is directed to a computerized medical care system for providing a medical pre-approval. The system includes a computing engine configured to receive a diagnosis code identifying diagnosis of a medical condition and a service code identifying a requested medical service; a medical diagnosis filter coupled to the engine and configured to display a question that should be considered in making the diagnosis of the medical condition, the medical diagnosis filter further being configured to prompt a user response to the displayed question, validate the diagnosis if the expected response matches the received user response, and invalidate the diagnosis if the expected response fails to match the received user response; and a plurality of medical procedure filters coupled to the engine and configured to determine a validity of the requested medical service relative to the diagnosis based on each of the applied medical procedure filters. The computing engine is configured to provide feedback based on the determination of the validity of the diagnosis and requested medical service. The feedback prompts modification of the diagnosis or medical service that is ultimately rendered to a patient if respectively the diagnosis or requested medical service is not validated.

It should therefore be appreciated that aspects of the present invention are directed to a system and a method for validating a diagnosis and medical service submitted by a provider, before such medical service is actually rendered. This helps protect the welfare of the patients. Furthermore, the likelihood of misdiagnosis is reduced, and the likelihood that the treatment delivered will help heal the patient is increased.

BRIEF DESCRIPTION OF THE DRAWINGS

These and other features, aspects, and advantages of the present invention will become better understood with regard to the following description, appended claims, and accompanying drawings, where:

FIG. 8 is a screen capture of a first procedure results interface in accordance with an exemplary embodiment of the present invention;

FIGS. 11A-11D are examples of response letters produced via a reporting interface according to an embodiment of the present invention;

FIG. 13 is a screen capture of a screen listing various organizations that a user may select in order to enable filters associated with the selected organizations according to one embodiment of the invention;

FIG. 15 is a screen capture of a graphical user interface listing various history based filters that may be enabled by a user according to one embodiment of the invention;

DETAILED DESCRIPTION

Figure 1:
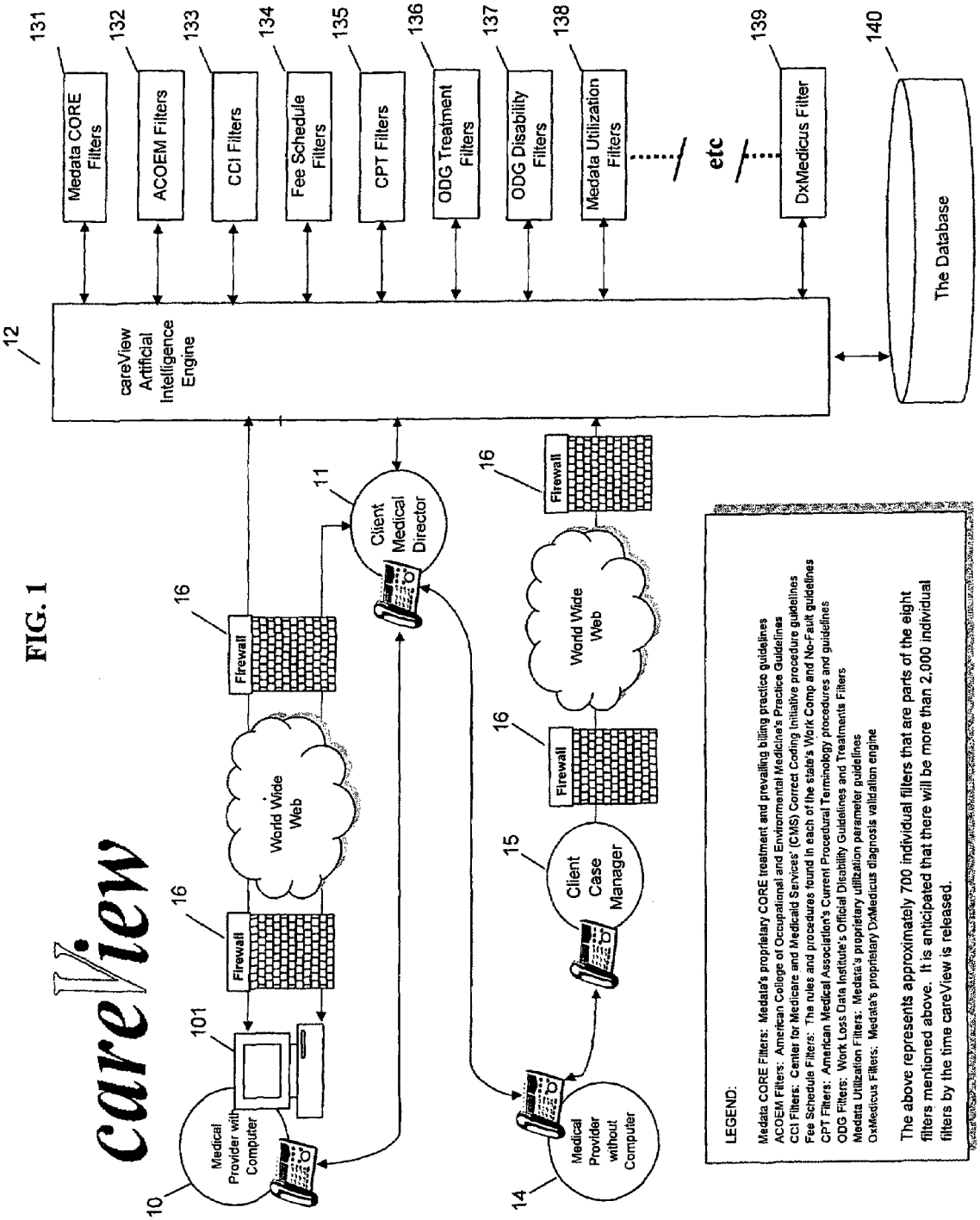
FIG. 1 is a functional block diagram of a computerized medical care system in accordance with an exemplary embodiment of the present invention.

Exemplary embodiments of the present invention are directed to providing a method and system for collecting and storing information and using the information to animate a computer application.

In accordance with an exemplary embodiment, an organizational structure for storing the information may be composed of elements that conform to a standardized programming language such as, for example, the extensible markup language (XML) specification. As is known in the art, XML is a markup language for documents containing structured information. Structured information contains both content (words, pictures, etc.) and some indication of what function that content performs.

Features of the present invention may be best understood in the context of a computerized medical care system that utilizes any of a variety of user interfaces. Such user interfaces may be invoked by or for a medical provider to provide to the medical care system, diagnostic code(s) and associated procedure code(s) for receiving pre-approval of respectively diagnoses and medical services identified by such codes.

In the context of computerized medical care systems, third-party payors and regulatory agencies often require that many (if not all) healthcare-related events and/or episodes be abstracted and described in summary fashion using a coding scheme that is specified in advance. To provide identifiers associated with various diseases and conditions, many coding schemes are in use and are suitable for this purpose. For example, the international classification of diseases (ICD) from the World Health Organization, the current procedural terminology (CPT) from the American Medical Association (AMA), and the systematic nomenclature for medicine (SNOMED) from the College of American Pathologists (CAP) are just a few of the currently available coding schemes that may be utilized to document primary diagnosis or prescribed medical procedures.

One skilled in the art will appreciate, however, that the present invention is not limited to medical record applications. Rather, the present invention is equally applicable to a variety of applications that require the contemporaneous retrieval of records that must be validated, e.g., to meet financial and/or policy-related requirements.

The computerized medical care system according to the various embodiments of the present invention provides validation of a diagnosis of a medical condition, validation of determined medical services, and/or validation of anticipated billings or charges for the determined medical services, that may be provided by a requesting entity (e.g. a medical service provider, case, manager, etc.) during a pre-approval session. In this regard, the medial care system invokes multiple filters, either in parallel or in sequence one after another, to determine the appropriateness of the diagnosis, medical service(s), and/or billings/charges (collectively referred to as medical care). The appropriateness of the medical care may be based on information gathered from a medical provider, information gathered from experts in the medical field, medical literature, and/or historical data on diagnoses, procedures, billings, and the like. According to one embodiment, the determination of whether the requested medical care is appropriate is made on the spot during the pre-approval session.

According to one embodiment of the invention, feedback is provided in real time with the validating of the diagnosis and the requested medical care. The feedback may be a message indicating approval/validation of a diagnosis, service, or billing. Alternately, the feedback may be a message or letter indicating that the medical care cannot be currently validated. If the diagnosis or medical care cannot be validated, the feedback includes the reasons for the failure to validate, and any supporting materials for the lack of validation. The feedback may also prompt the requesting entity to provide additional information to help support the medical provider's position as to why the medical diagnosis or care is appropriate.

The real-time feedback to the requesting device allows on the spot notification of whether a submitted diagnosis and medical service has been validated or not, such as, for example, within seconds after a request for the approval has been transmitted to the medical care system. In this manner, patients benefit from the system because the approval process does not delay the providing of needed medical care. Furthermore, the checking and validation of a diagnosis or a medical service to ensure that they are medically appropriate protects the patient from diagnosis or prescription errors. If such errors are made, the present medical care system provides instant feedback of the error to the medical provider, which prompts modification of the diagnosis and/or medical service, allowing for improved medical care for the patients.

Medical service providers also benefit from the current system. The validating of diagnoses and medical services before the services are actually rendered provides reassurance that the diagnoses and services are medically appropriate. Furthermore, the feedback of any errors that have been detected which prompts the medical provider to modify the diagnoses or services to be rendered minimizes the risk of malpractice lawsuits. This is different from prior systems which focus is on analyzing submitted codes for payment purposes after associated medical services have been rendered, but not appropriateness of services from a medical perspective for better medical care of the patient.

In addition to the above, the medical care system according to me embodiments of the present invention also allows medical service providers to get paid or reimbursed by managed care organizations. That is, because expected charges are included in the pre-approval request, and filters may be enabled to validate the requested charges, the providers are notified prior to the rendering of the services of the chances of any of the charges being denied. In this manner, the service provider may modify the charges and/or procedures if the charges are likely to be denied.

FIG. 1 is a simplified block diagram of an exemplary computerized medical care system according to an embodiment of the present invention. The system includes an artificial intelligence engine 12. In one embodiment, the engine 12 is implemented using a mainframe server. The engine 12 may utilize any of various filters to evaluate a claim that is submitted before a requested medical service is provided. The data filters may include, but are not limited to, CORE filters 131 for taking medical procedure codes and providing an allowance, American College of Occupational and Environmental Medicine (ACOEM) filters 132, correct coding initiative (CCI) filters 133, fee schedule filters 134, current procedural terminology (CPT) filters 135, official disability guidelines (ODG) treatment filters 136, ODG disability filters 137, and utilization filters 138. These filters are collectively referred to as medical procedure filters, and are invoked for determining the medical appropriateness of requested medical care based on various procedure rules. The system further includes one or more medical diagnosis filters referred to as DXMEDICUS filters 139 for validating or invalidating an entered diagnosis based on various diagnosis rules. The CORE filters and DXMEDICUS filtering software is commercially available from Medata, Inc, of Tustin, Calif.

The above-described filters are used to implement certain billing practices and/or procedure guidelines. Some of the filters may be used to implement practices and/or guidelines in conformance with certain industry standards. For example, the CPT filters may be used to implement practices and/or guidelines in conformance with the current procedural terminology (CPT) from the American Medical Association. Some of the filters may be designed to evaluate medical treatment and the impact of the treatment with respect to a claim submitted by a medical provider.

As such, the above-described filters may be implemented as one or more software modules. The modules may be executed by the engine 12 itself, or may be executed via in other computers (or computing devices) and/or servers interfacing with the engine 12. In this regard, the engine or other computing devices executing the engine includes a processor and a memory. The memory stores computer program instructions that are executed by the processor to receive a medical code (e.g. a diagnostic or procedure code), identify one or more enabled filters, generate a series of prompts associated with each enabled filter for gathering information specific to the diagnosis or medical service identified by the code, and validate the medical code or not, based on the received responses to the prompts. Exemplary applications of some of these filters will be described in more detail later.

The computerized medical care system also includes a database 140 storing information used by the above filters in determining validity of diagnoses and medical procedures submitted by the medical provider 14. Such information may include, for example, historical data of the procedures being performed for different diagnoses, historical data surrounding the conditions of rendering the procedures, historical data of charges being applied, and the like. The database may further correlate the gathered historical data to individual patients, doctors, and/or or organizations. Reports may then be generated based on the correlated data. For example, a report may be generated with information on how often a doctor's diagnoses and/or procedures fail to be validated upon application of the various data filters provided by the system. The ratio of invalid diagnoses to valid diagnoses may then be provided in the report.

Medical providers provide certain services to patients. With continued reference to FIG. 1, a medical provider 10 having direct access to a computer (or computing device) 101 can access (e.g., request information and receive information from) the engine 12, over a data communications network such as, for example, a local area network, private wide area network, or the public Internet. However, an individual or an entity not having direct access to a computer can access the engine through alternative routes.

For example, a medical provider 14 not having access to a computer can access the engine 12 via a client case manager 15, which, in turn, accesses the engine 12, via, for example, the World Wide Web. Here, the medical provider 14 may relay information to the client case manager 15, for example, in person or by telephone. The client case manager may then relay the information to the engine by way of the World Wide Web. Also by way of example, by virtue of its position, a client medical director 11 can also access the engine 12.

As shown in FIG. 1, the medical provider 10 and the client medical director 11 can interface with each other. Similarly, the medical provider 14 and the client medical director 11 can interface with one another.

To provide increased levels of security, interfaces between the computer 101 and the engine 12 and between the client case manager 15 and the engine 12 can be guarded and monitored using firewalls 16. It will be appreciated by one skilled in the art that any suitable firewalls (e.g., commercially available firewalls) may be used here. Further, one skilled in the art will appreciate that the number and types of computers may vary in accordance with the setting (e.g., clinical setting) of each application. For example, the computer 101 may be a standard desktop personal computer, a notebook-style computer, a personal digital assistant, or a mobile telephone.

The medical provider 10, 14 may use the above-described computerized medical care system before providing one or more services to a patient. Here, the medical provider 10, 14 enters certain pieces of information during a pre-approval session. In one embodiment, the pieces of information include: an identifier associated with (or corresponding to) the patient, an identifier associated with the medical provider 10, 14 providing the services, a particular condition(s) for which the medical provider 10, 14 is providing the services, the particular treatment(s) that the medical provider 10, 14 is proposing to use to treat the condition, and optionally, charges associated with the particular treatments.

In described exemplary embodiments, the computerized medical care system is utilized for determining whether a requested diagnosis or procedure is medically adequate. However, one skilled in the art will appreciate that the computerized medical care system may have other applications and can be used in other professions and/or industries having similar documentation or pre-approval requirements. Therefore, the described exemplary medical care systems are presented by way of illustration only and not by way of limitation.

Figure 2:
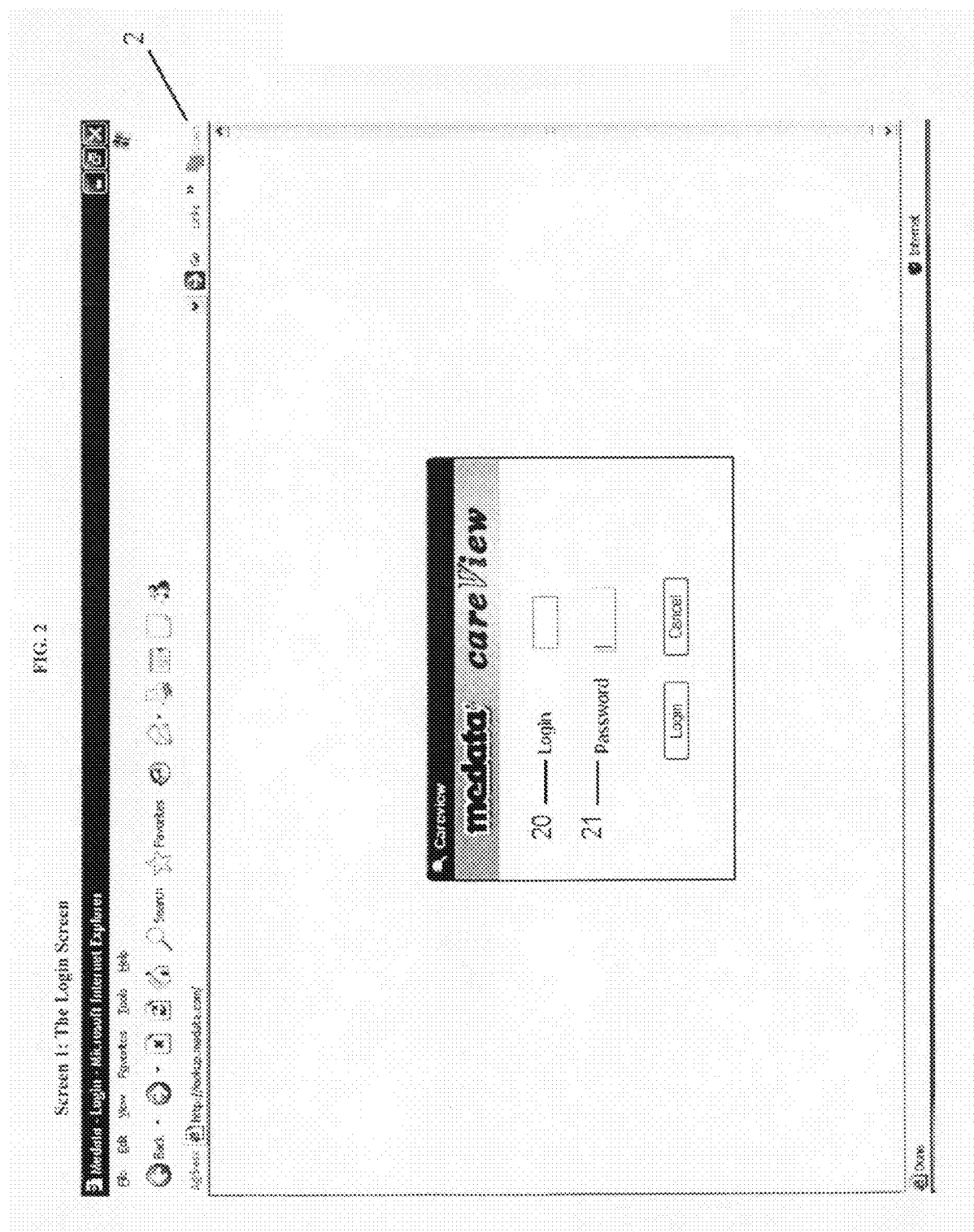
FIG. 2 is a screen capture of a login interface in accordance with an exemplary embodiment of the present invention.

With reference to FIG. 2, a provider 10 using the system is first prompted by the system to log on the computerized medical care system by entering identifiers on the login screen 2. The required identifiers may include a login ID 20 and a password 21.

The identifiers entered on the login screen 2 set forth the capabilities that will be bestowed to the provider using the system. In contrast with an administrator of the system (who is allowed to use a wide range of the capabilities of the system, including changing options within the system), the provider 10 may be allowed to use only a more limited range of capabilities, commensurate with the scope of the capabilities granted to it.

Figure 3:
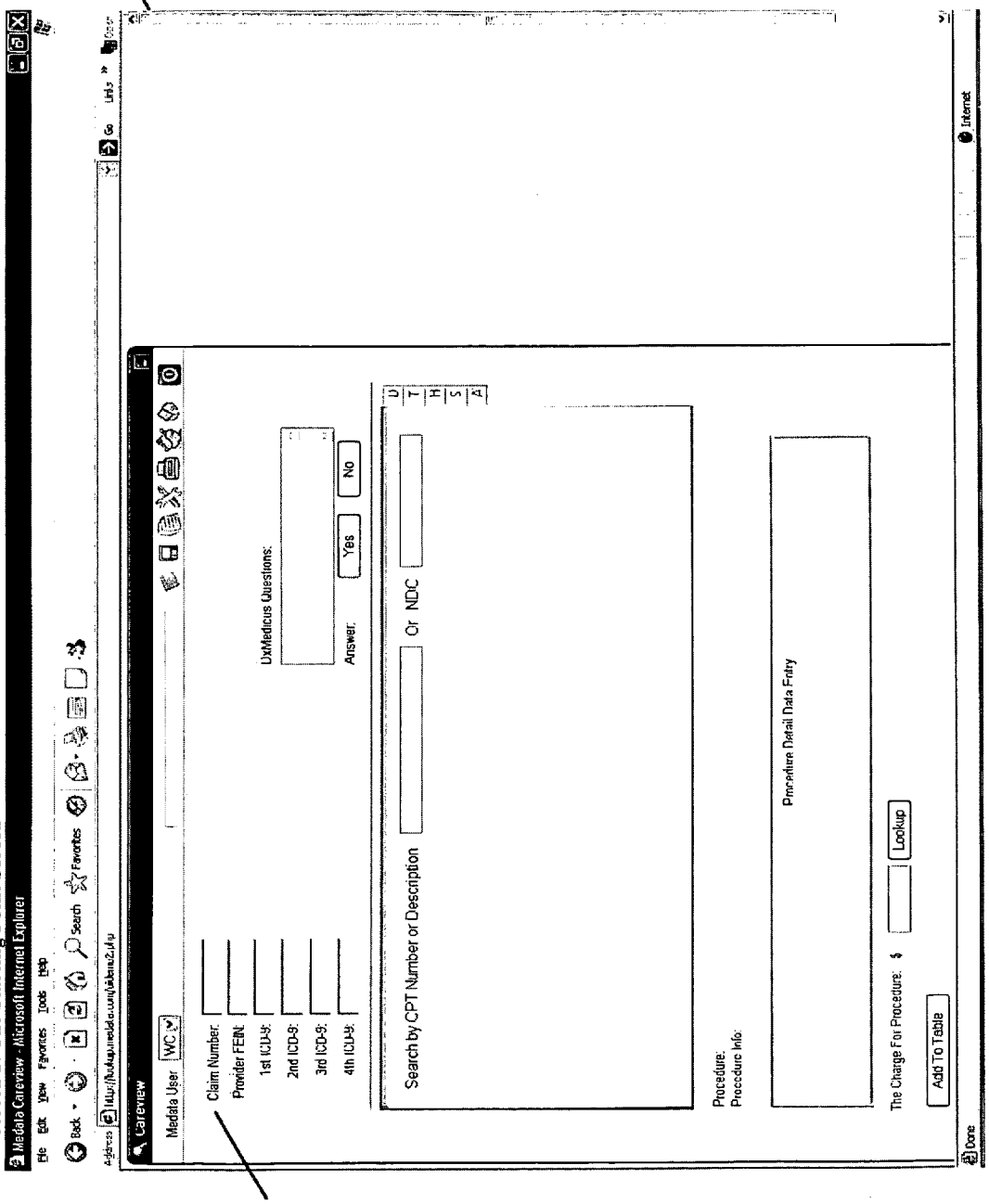
FIG. 3 is a screen capture of a starting interface in accordance with an exemplary embodiment of the present invention.

With reference to FIG. 3, after the provider 10 has entered a valid combination of login name 20 and password 21, the starting point screen 3 is displayed. Here, the provider 10 can enter information in any of various fields to seek authorization regarding a particular patient who is to be treated. For example, the provider 10 can enter a claim number 31 that is associated with (or corresponds to) the patient. As another example, the provider 10 can enter the name of the patient.

Figure 4:
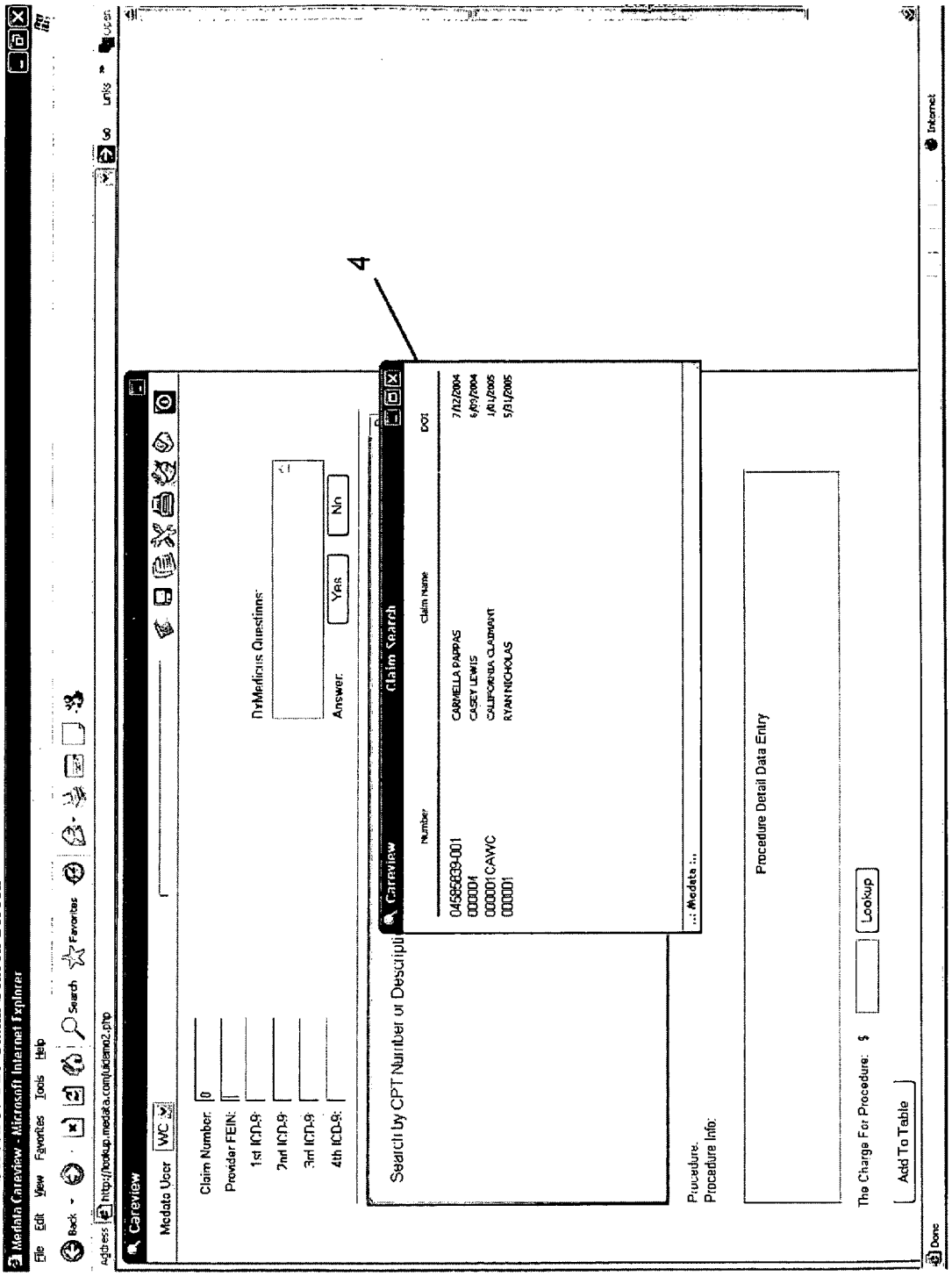
FIG. 4 is a screen capture of a claim search interface in accordance with an exemplary embodiment of the present invention.

If a claim number 31 (or a portion of a claim number 31) is entered, the name of the corresponding patient (or names of corresponding patients) is displayed. With reference to FIG. 4, after the provider 10 has entered a claim number 31 of "0," a claim search 4 is displayed. As shown in FIG. 4, the claim search 4 displays information relating to various patients associated with the entered claim number 31 of "0." For example, in one embodiment, patients associated with the entered claim number 31 of "0" are those patients who have a claim 31 beginning with the digit "0": "Carmella Pappas," "Casey Lewis," "California Claimant," and "Ryan Nicholas." Here, the provider can select any one of the displayed patients. Alternatively, the provider 10 can enter the name of the patient to retrieve any and all patients having the entered name.

Figure 5:
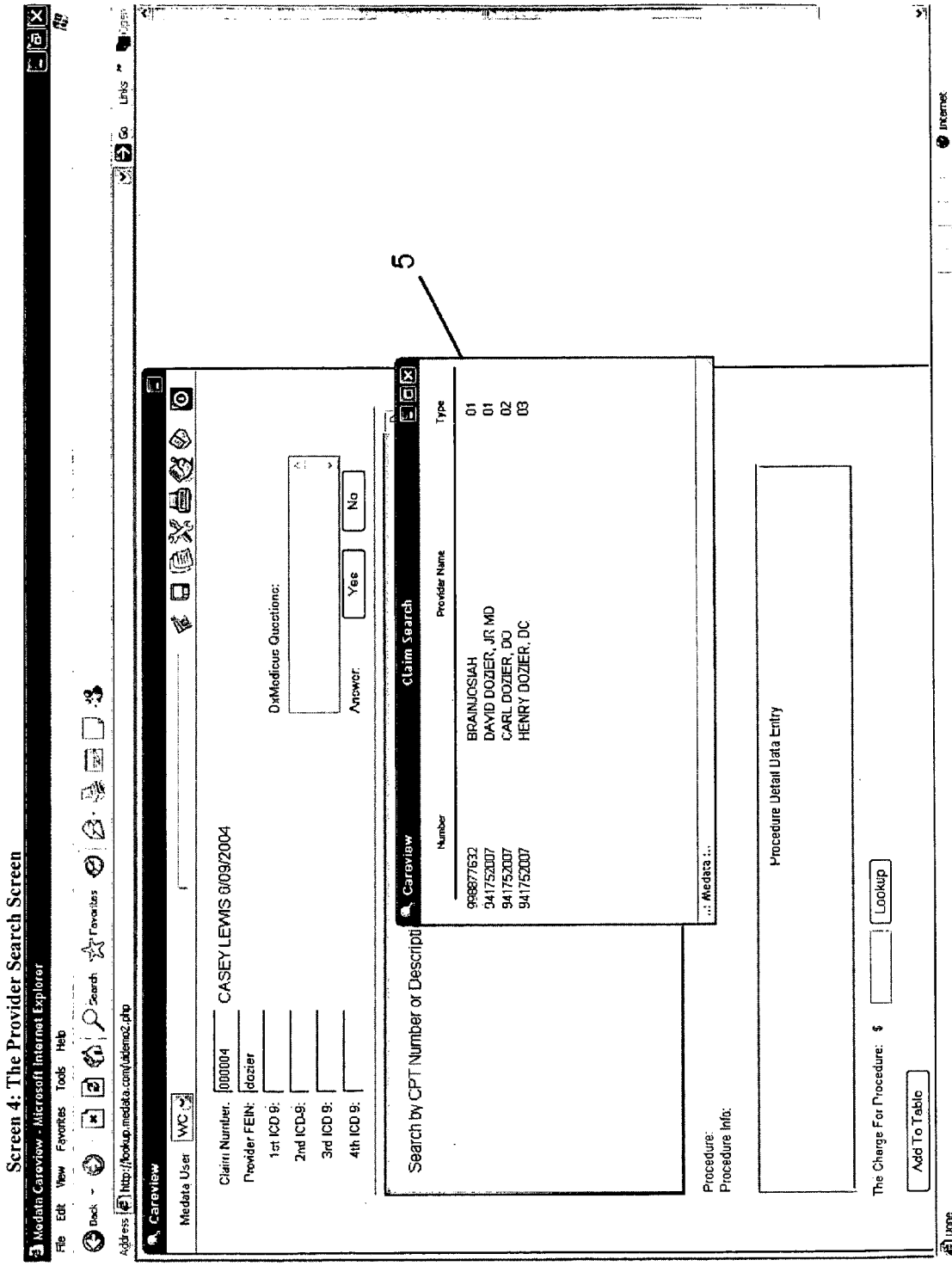
FIG. 5 is a screen capture of a provider search interface in accordance with an exemplary embodiment of the present invention.

With reference to FIG. 5, the patient "Casey Lewis" associated with the claim number 31 of "000004" is selected, and a provider search screen 5 is displayed. As shown in FIG. 5, the provider search screen 5 displays various providers associated with the patient "Casey Lewis": In one embodiment, the displayed providers are providers who have previously provided services to the patient.

As shown in FIG. 5, the displayed providers that are associated with "Casey Lewis" are: "Brainjosiah," "David Dozier, Jr MD" "Carl Dozier, DO" and "Henry Dozier, DC." Here, any one (or more) of the displayed providers can be selected such that more detailed information regarding the services previously provided by the one (or more) displayed provider will be displayed. In one embodiment, the provider 10 selects itself to retrieve information regarding the services that it previously provided to the patient. Alternatively, the provider 10 can enter, in the present screen, either an identifier associated with the provider (FEIN) or the name of the medical provider, which initiates a search screen.

Figure 6:
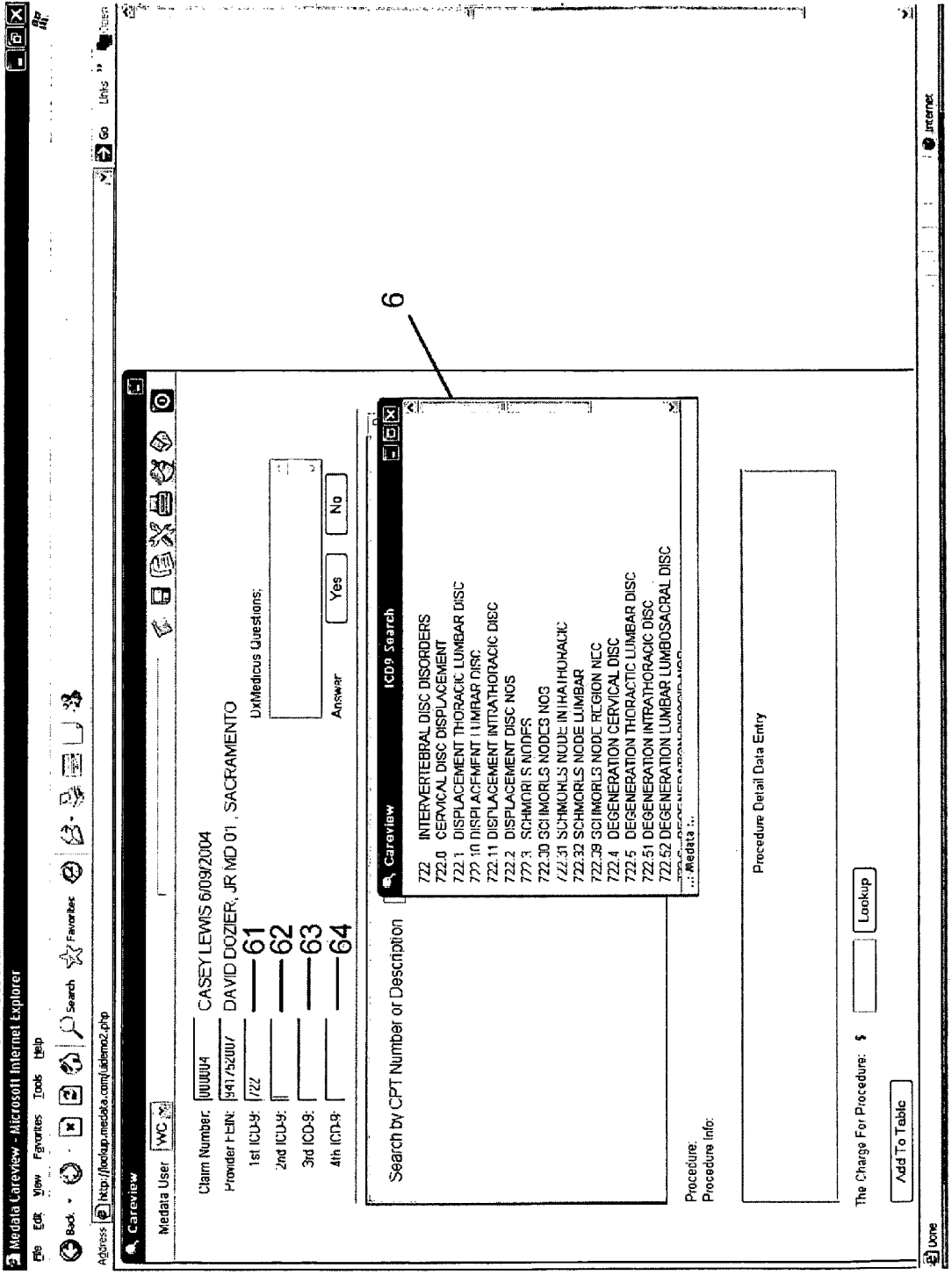
FIG. 6 is a screen capture of a medical code search interface in accordance with an exemplary embodiment of the present invention.

With reference to FIG. 6, different codes corresponding to various diagnoses (or conditions) are displayed on the ICD9 search screen 6. The ICD9 search screen 6 allows the provider 10 to select a specific condition for which the patient is requiring treatment by the provider 10. Here, as shown in FIG. 6, the selection can be performed by entering either a CPT number or one or more keywords pertaining to the condition. With reference to FIG. 6, entering the CPT number "722" in the 1st ICD-9 field 61 retrieves a list of conditions having CPT numbers starting with the numeric string "722," e.g., the condition "INTERVERTEBRAL DISC DISORDERS" having a CPT number of "722," the condition "CERVICAL DISC DISPLACEMENT," having a CPT number of "722.0," etc.

Although FIG. 6 shows that only one numeric string is entered in the field 61, the provider can enter additional numeric strings to select other conditions for which the patient is also requiring treatment. In more detail, these additional numeric strings can be entered in the 2nd ICD-9 field 62, the 3rd ICD-9 field 63, and the 4th ICD-9 field 64. Although up to four numeric strings can be entered in the embodiment shown in FIG. 6, one skilled in the art that additional fields can be implemented such that the provider 10 can select more than four corresponding conditions.

Figure 7:
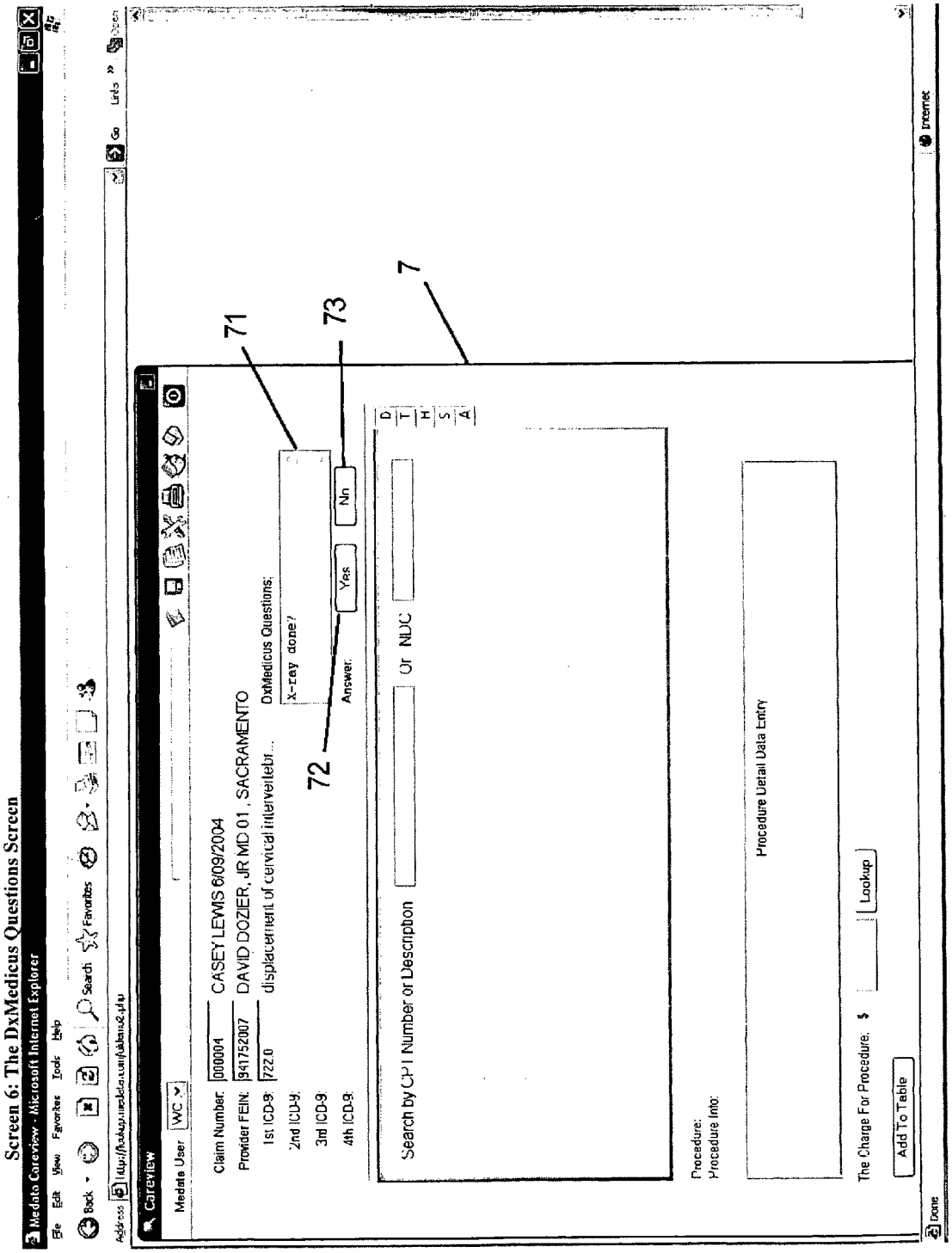
FIG. 7 is a screen capture of a validation interface in accordance with an exemplary embodiment of the present invention.

With reference to FIG. 7, the condition "CERVICAL DISC DISPLACEMENT" corresponding to the CPT number 722.0 is selected. Here, a series of questions are presented to the provider 10 in the questions field 71 of the DXMEDICUS Questions screen 7. These questions may be stored in and retrieved from the DXMEDICUS filter 139 (see, for example, FIG. 1). For example, in FIG. 7, the question presented to the provider 10 in the questions fields 71 is "X-ray done?" As such, the answer selections available to the provider 10 are "Yes" and "No" (selectable by clicking the button 72 or the button 73, respectively).

In one embodiment, only one question is presented to the provider 10 in response to the selected condition. However, in other embodiments, a series of more than one questions may be presented to the provider 10 for each of the selected conditions. The questions in the series may or may not be interrelated. That is, the answer provided to one of the questions may determine whether a first sub-series of questions or a second sub-series of questions will be presented to the provider 10.

In addition, although the buttons 72 and 73 correspond to "Yes" and "No," respectively, in the embodiment shown in FIG. 7, one skilled in the art can appreciate that the buttons 72, 73 can correspond to answer choices other than merely "yes" or "no." Further, one skilled in the art can appreciate that questions having more than two possible answer choices can also be implemented in the DXMEDICUS filter 139 and accordingly displayed on the DXMEDICUS Questions screen 7.

The questions displayed in the questions field 71 are directed to solicit information from the provider 10 for validating the diagnosis for which the treatment is directed. That is, the questions are configured to elicit information from the provider 10 that would aid in determining whether the diagnosis is medically appropriate. As such, each of the questions are questions that should be considered when the indicated diagnosis was made. The questions may be based, for example, on pieces of information collected from the international medical literature, which support algorithms designed to validate diagnoses. The display of the questions and prompting of a response by the medical provider forces the medical provider to consider these questions for more accurate diagnosis.

By way of example, a diagnosis of "Strain" or "Sprain of the Lumbar Region" (ICD 847.2) should not be made for patients who do not experience pain in the lower back and one of the following symptoms: tenderness to palpation; limitation of range of motion in the lumbosacral spine; and swelling. In other words, if the patient does not experience both pain in the lower back and any one of the above three symptoms, then a diagnosis of 847.2 for this patient is incorrect. Therefore, if submitted, such a diagnosis should not be validated. Information such as that described above may be implemented in the filters shown in FIG. 1, e.g., the DXMEDICUS filter 139.

Based upon the answers given to questions presented by the DXMEDICUS filter 139, a diagnosis is either validated or not validated. This feature of embodiments of the present invention ensures that the patient's welfare is protected. Accordingly, the likelihood of a misdiagnosis is reduced, and the likelihood that the treatment delivered will help to heal the patient is increased. If the diagnosis is not validated, then the system may address further questions to the provider, for example, in a formal report. Such a report may inform the provider 10 that the answers submitted do not support a finding that the diagnosis was valid.

With reference to FIG. 8, the data entry screen 8 for a first treatment or diagnostic procedure is displayed. Here, the system requests that the provider 10 enter a code that corresponds to a treatment that the provider is seeking to provide to the patient. The code may be in the form of a CPT procedure code, NDC drug code, HCPCS code, DRG code, or any other valid code for a medical service to be delivered (collectively referred to as procedure codes). The procedure codes utilized may originate from the fee schedule of the state or local jurisdiction in which the provider 10 is practicing, the AMA's CPT schedule, the HCPCS, ASA, ADA, etc. Similarly, the drug codes utilized may originate from the list of NDC numbers that identify each and every medication found within the Redbook or MediCal publications, as in standard for such purposes.

In embodiments of the present invention, the provider 10 enters information regarding the treatment sought to be provided via the field 81 (corresponding to "Procedure Code") or the field 82 (corresponding to "Procedure Desc."). By way of example, in the case of the field 81, the provider 10 can enter the CPT code "97010," which corresponds to Hot or Cold Packs. In the case of the field 82, the provider can enter all or some portion of the character string "HOT PACKS." If the string "HOT PACKS" is entered in field 82, then the system will return all of the procedure codes corresponding to descriptors that contain this particular string.

Similar to the treatment procedures described above, drug treatments can be entered in a similar manner. By way of example, to seek validation for administering aspirin to a patient, the provider 10 can enter the NDC number corresponding to aspirin in field 81, or enter the string "ASPIRIN" in field 82 to derive the NDC number for that particular drug.

Figure 9:
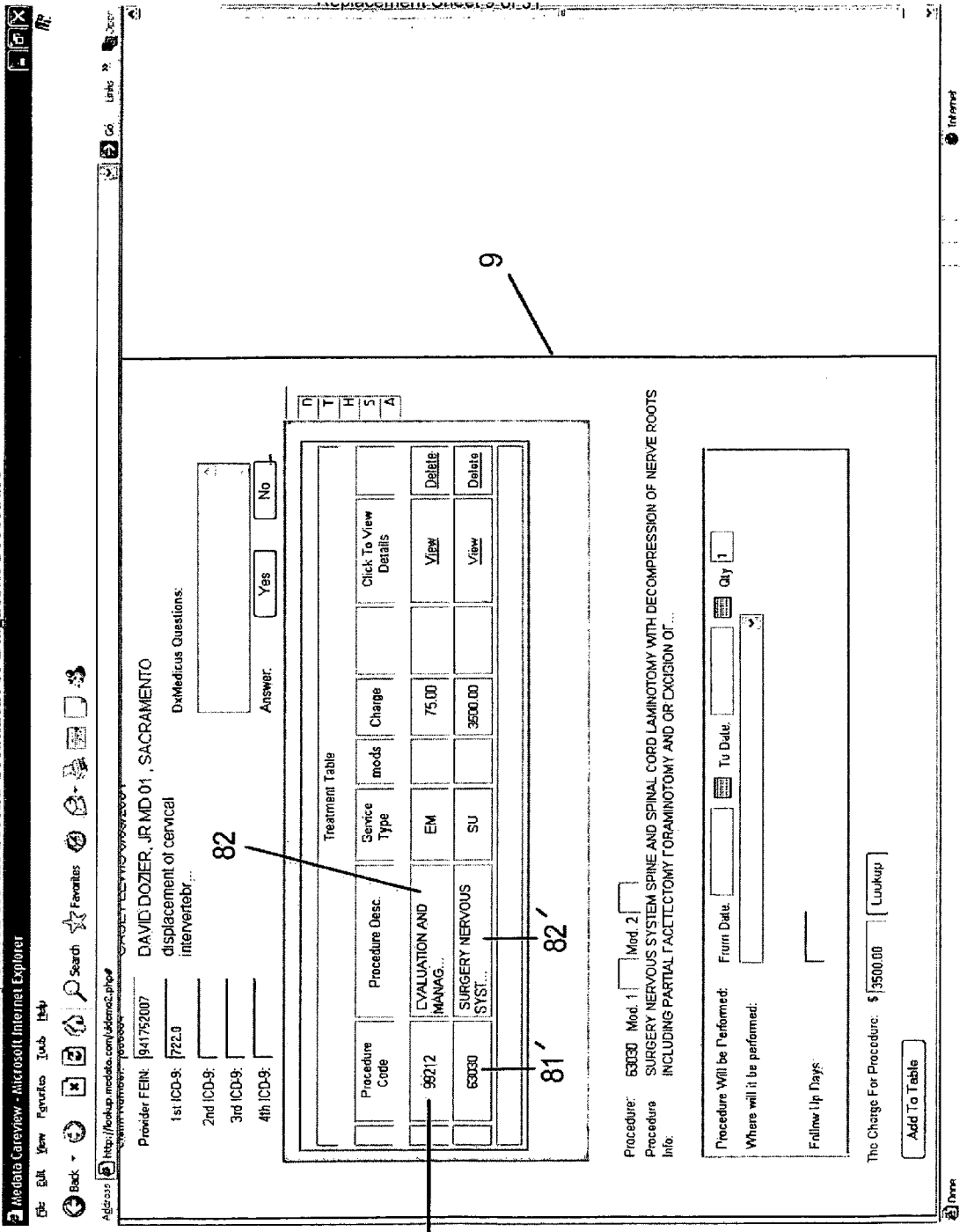
FIG. 9 is a screen capture of a second procedure results interface in accordance with an exemplary embodiment of the present invention.

Although only one submitted treatment is shown with reference to FIG. 8, the provider 10 can submit more than one treatment at a given time. For example, with reference to FIG. 9, a data entry screen 9 may be updated to receive additional treatments or diagnostic procedures. As shown in FIG. 9, the provider can enter information regarding a second proposed treatment or procedure in field 81', 82'. The fields 81', 82' are substantially similar to the fields 81, 82 and, as such, will not be described in more detail below.

One skilled in the art will appreciate that the system can be configured to accept any number of treatments or diagnostic procedures that the provider 10 wishes to submit in a manner similar to those described above.

After a code is entered, the engine 12 generates a series of prompts associated with the entered code based on the filters that have been enabled. One or more of such prompts help quantify and describe the specific service being requested. For example, if CPT code 97010 (Hot/Cold Packs) is entered as a method of treatment, the engine 12 requests information that is specific to Hot/Cold Packs. The Hot/Cold Pack procedure code prompts may require information regarding a date range for rending the services, date frequency, and charges being requested. As another example, if a provider requests the use of pharmaceuticals, the engine prompts for an NDC number, the number of doses to be dispensed, the frequency in which the drugs should be taken, number of pills to be dispensed, or the like. The answers to the questions may then be used by the enabled filters for determining that the requested medical service is medically appropriate, and validating the requested service.

Reports generated by the system or a separate system as feedback to a medical provider upon evaluation of a submitted diagnosis and requested medical care will now be described in more detail with reference to FIGS. 10-11D. According to embodiments of the present invention, a computerized medical care system may interface with a registration or billing system to automatically generate electronic and/or hardcopy documents including authorization information. In one embodiment, the document includes information that uniquely identifies the subject of the document.

Once the provider 10 has entered a request, the request may be electronically transferred to a bill review engine. After the request is received, only those services that are pre-authorized will be paid. Because, as described previously, the pre-authorization process may be completely paperless, the process may become seamless, virtually eliminating the possibility of records getting lost or misdirected.

As described above, embodiments of the present invention are directed to a web-enabled, user-friendly application that allows for the entry of provider treatment plans. The described embodiment includes a series of filters, each of which is designed to evaluate medical treatment and the impact of the treatment on a specific claim. For instance, one of the filters may effectively compare the submitted procedures for a given patient having a certain diagnosis with the procedures historically provided to other patients having the same (or substantially the same diagnosis). By way of example, if the treatment being requested is observed in only one out of every 10,000 cases involving the same diagnosis, then the provider 10 is asked by the system to describe the medical necessity of providing the proposed treatment, in light of the rare nature of that particular treatment.

One skilled in the art will appreciate that, according to an embodiment of the present invention, hundreds of different filters may be implemented, over and above the CCI and ODG guidelines, to evaluate treatment plans. An evaluation is made, using artificial intelligence with little to no human decision-making. The response of the system may be nearly instantaneous in notifying the provider regarding the proposed treatment plan.

For example, the system may submit an email to the provider 10 within ten seconds, either authorizing care or raising questions that require additional information from the provider 10 before authorization can be granted. That is, embodiments of the present invention are designed to either authorize a submitted procedure or obtain information from the provider 10 that would demonstrate the medical necessity of the procedure being submitted for the condition being treated. If the provider 10 is unable to provide the necessary additional information, then authorization is not granted for performing the procedure.

Figure 10:
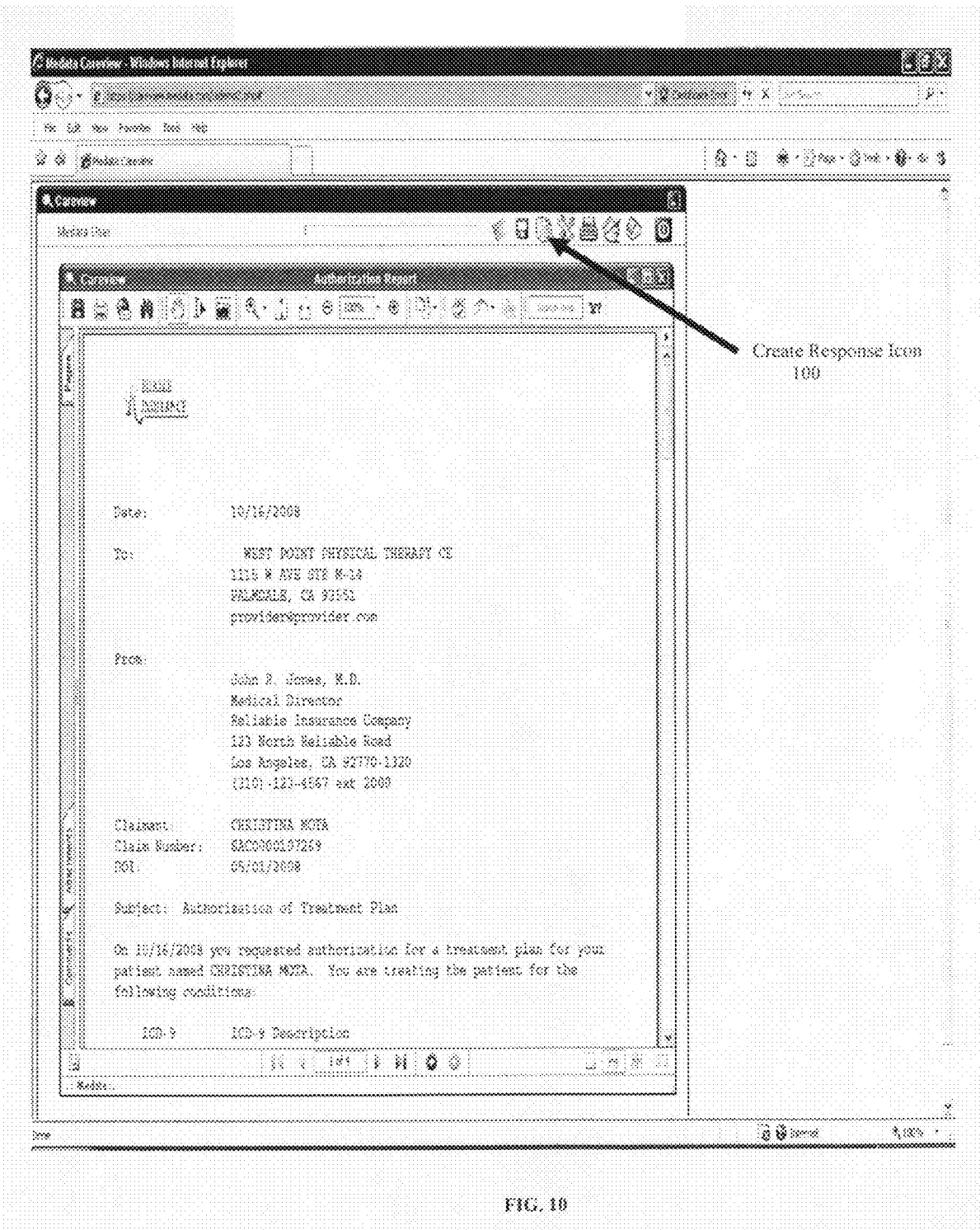
FIG. 10 is a screen capture of a reporting interface according to one embodiment of the invention.

FIG. 10 is a screen capture of a reporting interface according to one embodiment of the invention. The interface includes a "create response" icon 100 which is actuated for generating a letter that is responsive to a pre-approval request.

FIGS. 11A-11C is an example of a response letter produced upon actuation of the "create response" icon 100 according to one embodiment of the invention. As shown in FIGS. 11A-11C, a provider has requested authorization to perform two procedures: "SURGERY NERVOUS SYSTEM SPINE AND SPINAL CORD LAMINOTOMY WITH DECOMPRESSION OF NERVE ROOTS INCLUDING PARTIAL FACETECTOMY FORAMINOTOMY AND OR EXCISION OF HERNIATED INTERVERTEBRAL DISK ONE INTERSPACE LUM" (corresponding to a CPT Code of 63030) and "EVALUATION AND MANAGEMENT OFFICE OR OUTPATIENT VISIT NEW PATIENT WITH DETAILED PROBLEM FOCUSED HISTORY EXAMINER DECISION MAKING OF LOW COMPLEXITY 30 MINUTES" (corresponding to a CPT Code of 99203). As also shown in FIGS. 11A-11C, the provider requested a fee of $5000 for the first procedure and a fee of $200 for the second procedure.

With further reference to FIGS. 11A-11C, the system responds to the provider's request. Here, the system authorized the procedures because the provider satisfied the criteria (as implemented, for example, in one or more filters, with reference to FIG. 1) demonstrating the medical necessity of the diagnosis, and the system confirmed the validity of the diagnosis determined by the provider. In addition, the system performed an analysis of the fees proposed by the provider in view of allowances set forth by one or more groups of industry standards. For example, the allowances may arise from California's Official Medical Fee Schedule N (OMFS). As another example, as shown in FIGS. 11A-11C, the allowances may arise from the Official Medical Fee Schedule (OMFA) of the California Workers' Compensation Division of Industrial Injuries and established by the Administrative Director of the Division, pursuant to Sections 5307.1 and 5307.3 of the California Labor Codes.

With continued reference to FIGS. 11A-11C, because the fees proposed by the provider exceeded the identified allowances (i.e., an allowance of $994.47 for the procedure corresponding to CPT 63030 and an allowance of $102.37 for the procedure corresponding to CPT 99203), the system authorizes payments in amounts consistent with the allowances. In addition, it also offers the provider an opportunity to disclose any services that it has rendered that may go beyond the services typically associated with the submitted procedure. Here, if the provider is able to supply such information, which supports authorization of further payment(s), then the provider may do so.

FIG. 11D is an example letter generated as feedback to a medical provider with respect to multiple submitted diagnoses. The letter indicates that the responses to the questions that were displayed by the engine are not consistent with answers that would validate the diagnoses. According to one embodiment of the invention, the letter may be accompanied with journal articles that were used in framing the questions that were asked. The letter further requests that the medical provider provide additional medical information used in making the diagnoses, allowing the medical provider to defend the diagnoses that were made.

According to one embodiment of the invention, a letter that fails to validate a diagnosis or requested medical service is configured to prompt modification of the diagnosis or medical service that is ultimately rendered to a patient. In this manner, any errors made by the medical provider is corrected before the requested medical service is actually rendered to the patient.

Any of the filters described herein can either be turned on or off, based upon a client's specifications. Additionally, the several hundred filters associated with Medata's CORE filters 131 can also be turned on or off either individually or as a group or two or more of the filters.

Figure 12:
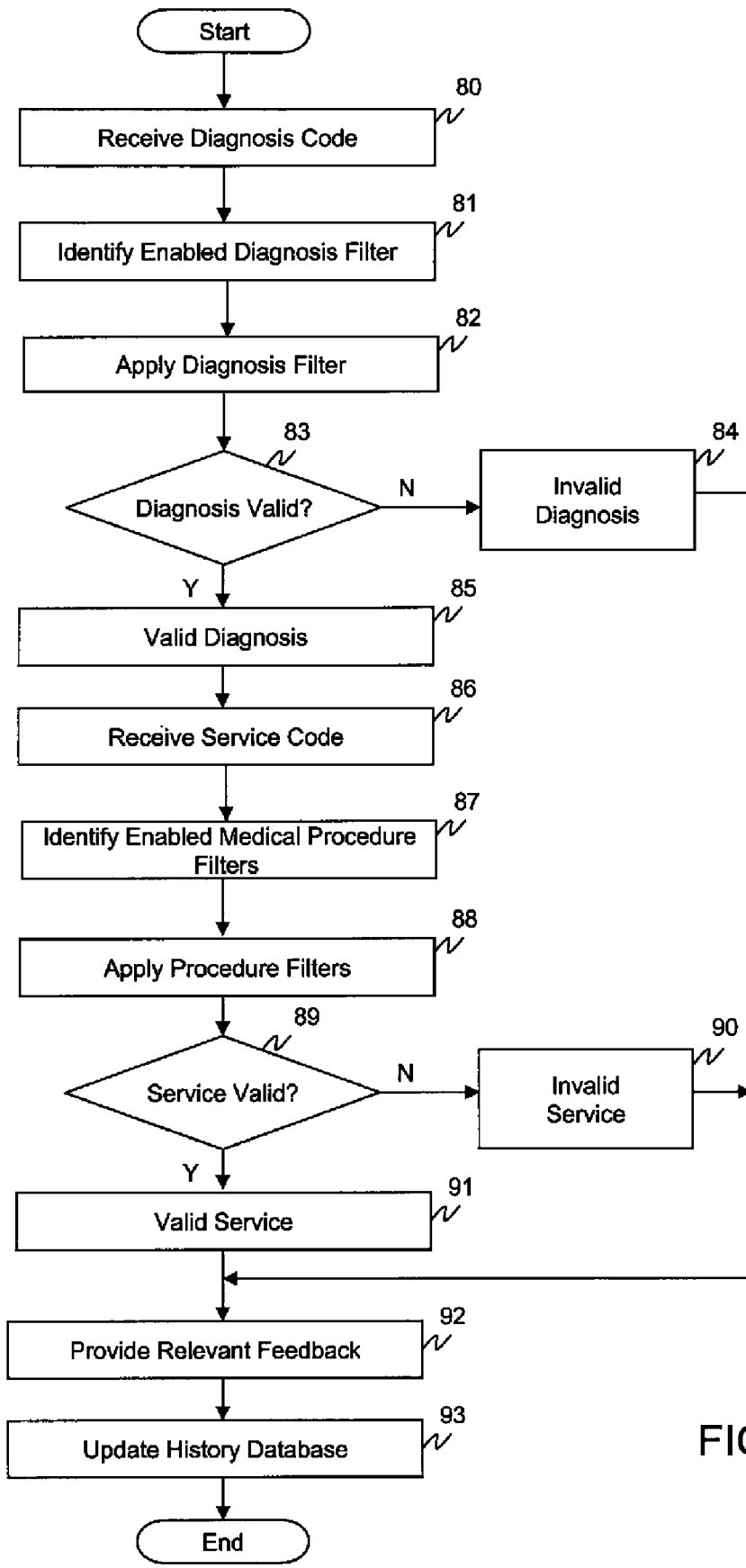
FIG. 12 is a flow diagram of a pre-approval process according to one embodiment of the invention.

FIG. 12 is a flow diagram of a pre-approval process executed by the engine 12 according to one embodiment of the invention. The process may be implemented by a processor hosted by the engine 12 according to computer program instructions stored in a memory that is coupled to the processor. The steps in the process may be executed in the order shown, or in any other order that will be appreciated by a person of skill in the art The process starts with a requesting device (e.g. the medical provider 10 or client case manager 15) initiating a pre-approval session. In step 80, the engine receives one or more diagnosis codes from the requesting device. Each code may be entered via a graphical user interface such as the one illustrated in FIG. 6.

In step 81, the engine identifies the enabled diagnosis filter (e.g. the DxMedicus Filter 139).

In step 82, the engine applies the enabled diagnosis filter for the received diagnosis code(s).

In step 83, a determination is made as to the validity of the diagnosis based on the applied medical diagnosis filter. In this regard, the engine determines whether the submitted diagnosis is medically appropriate based on information gathered from experts in the medical field, medical literature and research, and the like.

If the diagnosis is medically appropriate, the diagnosis is deemed valid in step 85. Otherwise, the diagnosis is deemed invalid in step 84.

In step 86, the engine receives a service code(s) identifying a requested medical service(s). The service code may be entered via a graphical user interface such as the one illustrated in FIG. 8. Other conditions relating to the rendering of the service may also be entered via the graphic user interface illustrated in FIG. 8.

In step 87, the engine identifies one or more enabled medical procedure filters. Such filters may include, for example, filters 131-138 illustrated in FIG. 1.

In step 88, the engine applies each of the procedure filters for the received service code.

In step 89, a determination is made as to the validity of the requested medical service relative to the diagnosis that was made based on each of the applied medical procedure filters. In this regard, the engine determines whether the requested service or a condition relating to the service is medically appropriate in light of the diagnosis that was made.

If the requested service is medically appropriate, the service is deemed valid in step 91. Otherwise, the diagnosis is deemed invalid in step 90.

After the validity of the diagnosis and requested services are determined during the pre-approval session, the engine proceeds to provide feedback to the requesting device of the determination. According to one embodiment of the invention, the feedback is provided during the pre-approval session, substantially contemporaneous with the validity determinations. The feedback may be in the form of a letter addressed to the medical service provider which is generated and displayed upon selection of the create response icon 100 (FIG. 10). The letter may also be emailed to the medical service provider or transmitted via any other data communications medium as may be conventional in the art. The instant feedback to the medical service provider prompts the on-the-spot adjustment by the provider of the diagnosis and/or medical service to be rendered, resulting in improved and more efficient service and care for the patients.

Below are more detailed descriptions of the filters supported by the computerized medical care system according to one embodiment of the invention.

Organization Based Filters

According to one embodiment of the invention, a plurality of filters are provided under an organizational category for implementing rules, suggestions, and protocols by organizations such as, for example, ACOEM, medical societies, specialty groups, chiropractic organizations, osteopathic organizations, the Federal Government, and the like, which control the delivery of medical care. The rules and suggestions by these organizations are valuable and frequently followed as guidelines for appropriate medical care. According to one embodiment, every rule, and suggestion, found in these publications are incorporated into one or more filters provided by the computerized medical care system as rules and suggestions that should be followed by medical practitioners treating patients.

Figure 13:
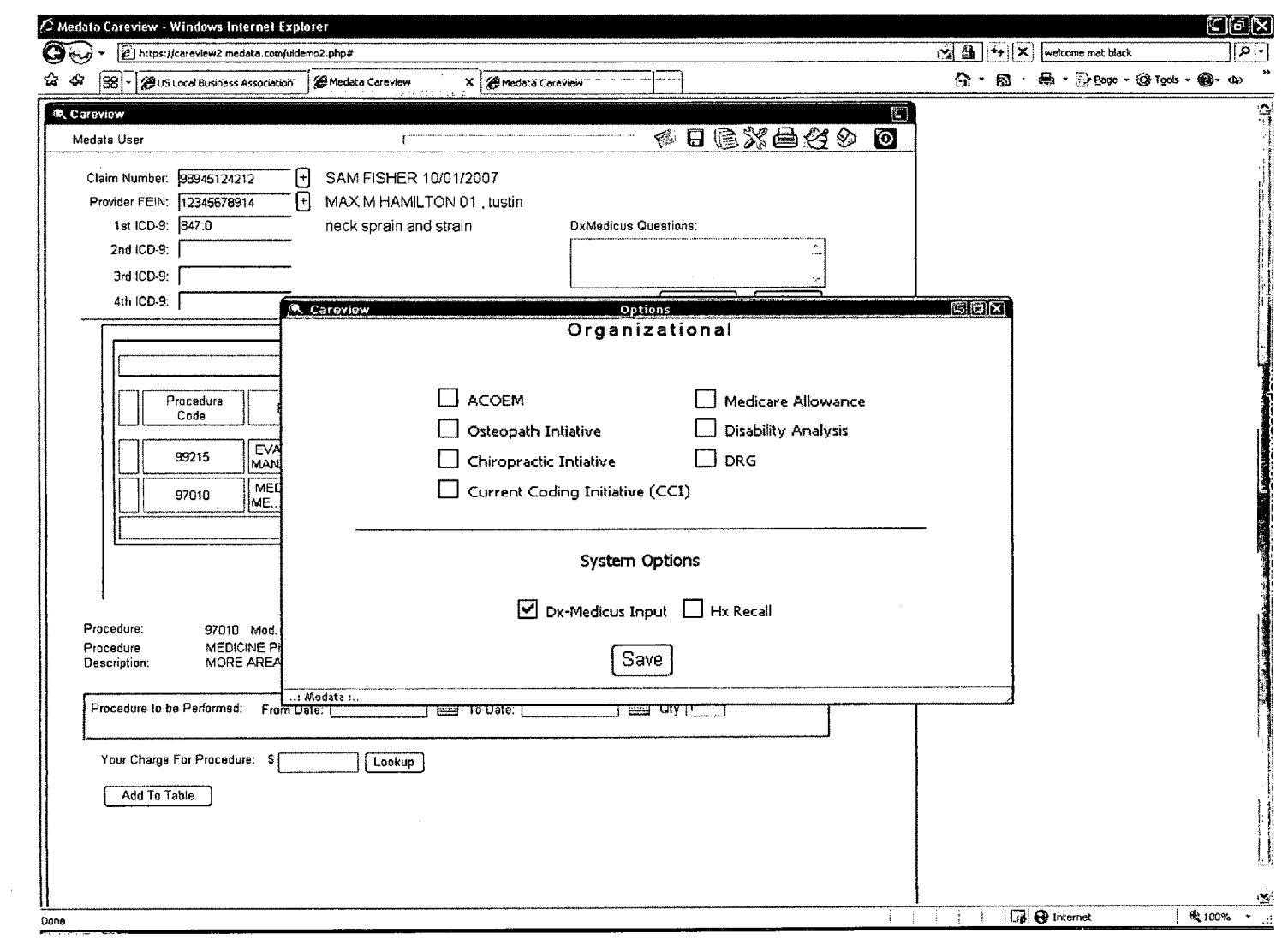

FIG. 13 is a screen capture of a screen listing various organizations that a user may select in order to enable filters associated with the selected organizations according to one embodiment of the invention.

ACOEM

One exemplary organizational filter provided by the computerized medical care system is an ACOEM filter, which incorporates rules that were established by the American College of Occupational and Environmental Medicine (ACOEM), $2^{nd}$ Edition. All the applicable rules in Chapters 8 through 14 which applies to information contained within the publication relative to the appropriate treatments and procedures for workers' compensation/industrial injuries are implemented by the ACOEM filter.

The State of California adopted the ACOEM guidelines as part of the California Code of Regulations, Chapter 4.5 Division of Workers'Compensation, Subchapter 1. Administrative Director—Administrative Rules, Article 5.5.2 Medical treatment utilization schedule, §9793.21 Medical Treatment Utilization Schedule, (a)(1) (http://www.dir.ca.gov/t8/9792_21.hmt.).

More than one hundred rules that were created by the Association are valid measures for appropriate medical care for various medical injuries. These rules are implemented by the ACOEM filter for being applied to procedure codes in the Current Procedural Terminology (CPT) and diagnostic codes as listed within the International Classification of Diseases, Revision 9 (ICD-9).

For example, a Chiropractor may request to perform chiropractic manipulation for a workers' compensation patient with a neck sprain 3 months after the date of injury. The computer software then queries the system to analyze whether the procedure is appropriate for the condition, and whether the procedure is appropriate in the time frame the services are rendered. On page 181 of the ACOEM Guidelines is found the following information in Table 8-8:

TABLE 8-8

Summary of Recommendations for Evaluating and
Managing Neck and Upper Back Complaints

| Clinical Measure | Recommended | Optional | Not Recommended |
|---|---|---|---|
| Physical treatment methods | | Physical manipulation for neck pain early in care only (B) At-home applications of heat or cold (D) Radio-frequency neurotomy (C) | Traction (B) TENS (C) Other Modalities (D)" |

Since the request for manipulation from the provider is made late in the therapeutic period, there really is no apparent justification for the proposed therapy. This therapy is optional ONLY if performed "early in care". Therefore, the engine 12 is configured to send an email to the provider requesting additional information which could justify the medical necessity for therapy that is unsupported by the ACOEM guideline.

Correct Coding Initiative (CCI)

Another organizational filter provided by the computerized medical care system is a Correct Coding Initiative (CCI) filter. The CCI edits were created by the Federal government to promote national correct coding methodologies and to control improper coding leading to inappropriate payment in Part B claims. These edits were developed utilizing coding policies based on coding conventions defined in the American Medical Association's CPT Manual, national and local policies and edits, coding guidelines developed by national societies, analysis of standard medical and surgical practices, and a review of current coding practices.

The CCI filter applies these rule sets to prevent improper payment when incorrect code combinations are reported. There are approximately 440,000 separate CCI edits used by the CCI filter. Below is a description of a few of those edits:

| Column 1 | Column 2 | CCI INSTRUCTIONS |
|---|---|---|
| 13151 | 13153 | Pay 13151 and Deny 13153 |
| 20000 | 20005 | Pay 20000 and Deny 20005 |
| 30000 | 30020 | Pay 30000 and Deny 30020 |
| 71260 | 36000 | Pay 71260 and Deny 36000 |
| 86890 | 99203 | Pay 86890 and Deny 99203 |
| 99203 | 43752 | Pay 99203 and Deny 43752 |
| etc. | | |

For example, the above information means that procedures 13151 and 13153 are an improper coding combination. In this specific case, procedure code 13153 should not be allowed.

Osteopathic Initiative

Another organizational filter provided by the computerized medical care system is an AOA filter. The American Osteopathic Association (AOA) publishes an initiative which provides osteopathic physicians with appropriate guidelines. According to one embodiment of the invention, all the AOA guidelines are applied by the AOA filter.

Chiropractic Initiative

A further organizational filter provided by the computerized medical care system is an ACA filter. The American Chiropractic Association (ACA) publishes an initiative which provides chiropractic physicians with appropriate guidelines. According to one embodiment of the invention, all the AOA guidelines are applied by the AOA filter.

Medicare Allowance

Another organizational filter provided by the computerized medical care system is a Medicare allowance filter. The Medicare allowance filter applies Medicare allowance recommendations consistent with a RBRVS method of payment. The RBRVS method of payment includes variables related to the following formula:

$$[((RVUW \times Budget\ Neutrality\ CF) \times RVZW) + (RVUE \times RVZE) + (RVUP \times RVZP)] \times CF$$

where each variable is defined as follows:
RVUW=Physician's WORK relative value units assigned to the procedure code
RVUE=Physician's EXPENSE relative value units assigned to the procedure code
RVUP=Physician's MALPRACTICE relative value units assigned to the procedure code
RVZW=Geographic WORK relative value units assigned to the provider's Medicare Locality
RVZE=Geographic EXPENSE relative value units assigned to the provider's Medicare Locality
RVZP=Geographic MALPRACTICE relative value units assigned to the provider's Medicare Locality
CF=Medicare Conversion Factor If the provider submits an invoice for an amount greater than that mandated by Medicare, then the provider is notified of this fact prior to the services being rendered. This is important to the provider and to the user, in that it clarifies cost considerations in the delivery of medical services and prior to those services being rendered.

Disability Analysis

Another organizational filter provided by the computerized medical care system is a disability analysis filter based on guidelines provided by "*The Official Disability Guidelines* (ODG)" which is published by Work Loss Data Institute (WLDI). The ODG contains lost time guidelines based upon actual data as opposed to expert opinion. For example, if a patient is placed on disability that far exceeds those experienced by other patients treated for the same condition, the disability analysis filter applies the real world example and requests an explanation from the provider for the necessity for the prolonged disability. The system provides a communication to the provider requesting specific information to justify the prolonged disability.

DRG

Another filter provided by the computerized medical care system is a Correct Coding Initiative (CCI) filter. The Diagnosis Related Group (DRG) system was designed by the Federal Government to control runaway charges for inpatient hospitalization. It was originally proposed in the early 1980's and has been accepted universally for Medicare. Additionally, many state agencies have implemented a DRG method of reimbursement for inpatient hospital stays. Currently, 14 states utilize modified DRG systems to control costs. According to one embodiment, all of the DRG information is included in the DRG filter. For example, a hospital provider recommending a patient for hospitalization is notified before being hospitalized of the DRG allowance for the condition for which the patient is being hospitalized. In addition to the allowance, the system notifies the provider of the DRG utilized and request the provider submit information justifying the additional charges.

DxMedicus

The DXMEDICUS filter provides a graphical user interface that allows medical providers, or claims handlers taking calls from the providers, to enter diagnostic information (ICD-9 codes) into the engine 12. The DXMEDICUS filter prompts the user with a series of questions based on the provider's diagnosis. Each of the questions are questions that should be considered whenever a particular diagnosis is made.

Each of the diagnoses in the ICD-9 that are used in indemnity and other types of cases have been formalized to form a computerized algorithm which either confirms or questions the validity of the diagnosis. According to one embodiment, the DXMEDICUS algorithms do not make a diagnosis, but rather, validates or invalidates the provider's diagnosis.

Figure 14A:
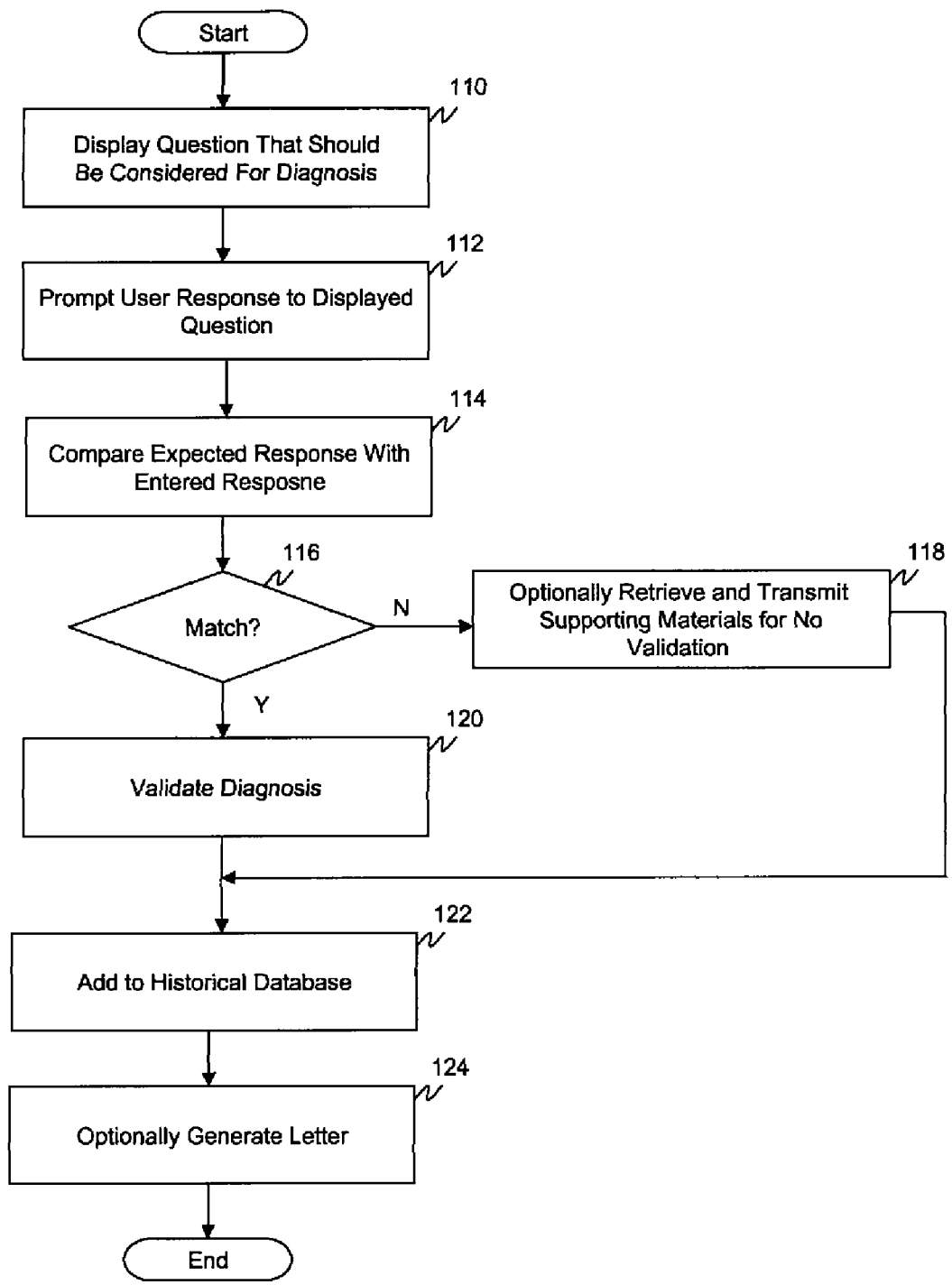
FIG. 14A is a flow diagram of a process for validating a medical diagnosis according to one embodiment of the invention.

FIG. 14A is a more detailed flow diagram of step 82 (FIG. 12) of applying the DXMEDICUS filter 139 for validating a medical diagnosis according to one embodiment of the invention.

In step 110, the filter displays a question that should be considered in making the diagnosis of the medical condition. In this regard, the filter identifies the specific diagnosis code and retrieves the questions that have been correlated to the code from the database 140.

In step 112, the filter prompts a user response to the displayed question as is illustrated in FIG. 7.

In step 114, the filter compares the expected response with the entered response. In this regard, the filter retrieves the expected answers that have been stored in the database 140 for each displayed question for the specific diagnosis.

If there is a match, as is determined in step 116, the diagnosis is validated in step 120. Otherwise, the diagnosis is not validated in step 118, and materials supporting the lack of validation may be optionally retrieved from the database 140 and provided to the medical service provider along with a response letter. That is, if the provider questions the decision of the DXMEDICUS filter, the system is configured to retrieve journal articles on the diagnosis in question, and transmit those articles to the medical provider via, for example, email, and further request that the medical provider submit articles that support his contention.

According to one embodiment of the invention, a medical provider's responses to the displayed prompts are recorded and stored in a historical database maintained in the database for future reference, as is reflected in step 122. Such information may be correlated to specific patients to which the requests relate, specific doctors making the diagnosis and request, and the like.

In step 124, a letter may be optionally generated indicating that the diagnosis has been validated or not. According to another embodiment, unlike the other filters within the system, the DXMEDICUS filter does not authorize or request additional information from the provider. The validation or lack thereof is stored in the historical database for later generating of reports based on a user command.

Figure 14B:
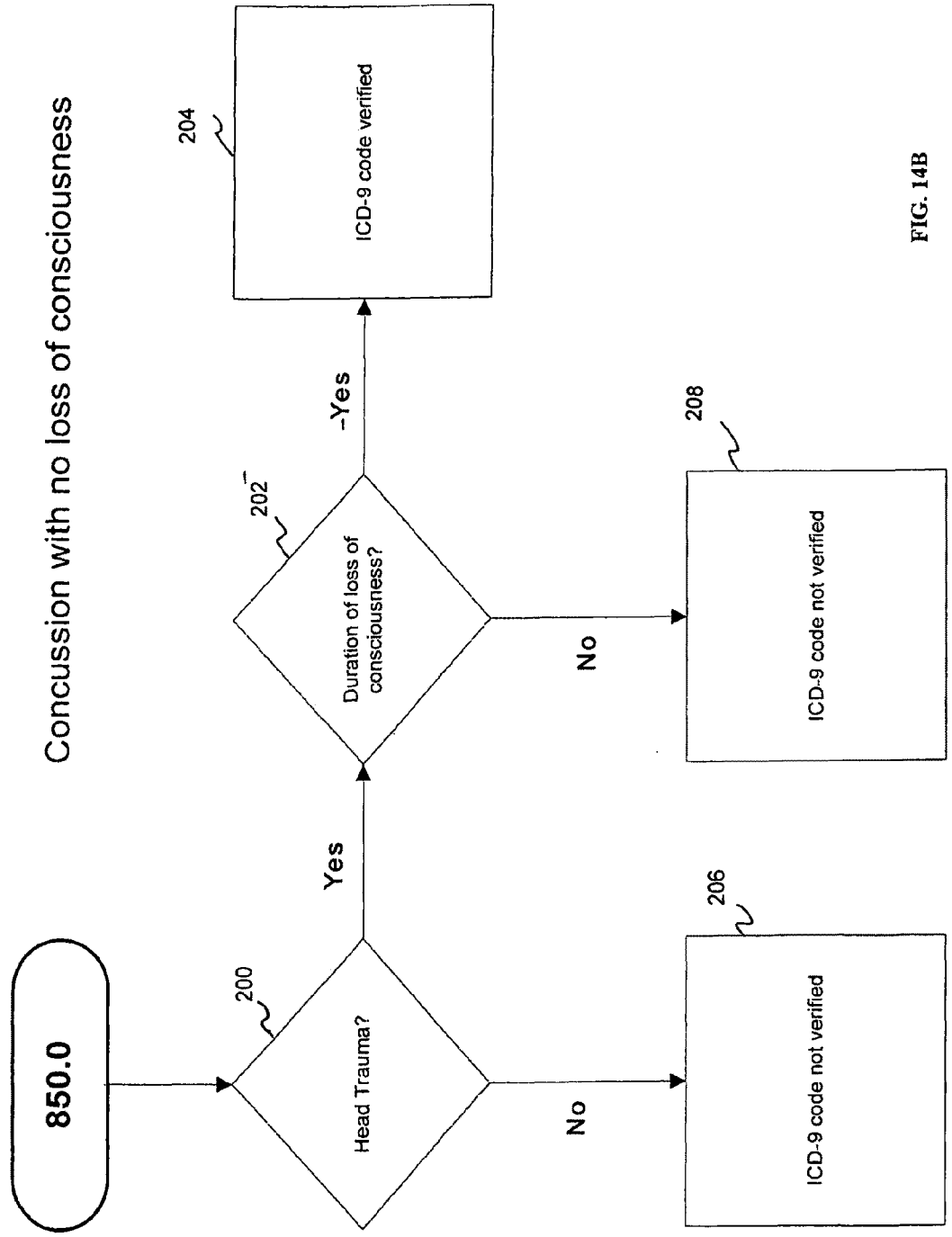
FIG. 14B is a flow diagram of a process for validating a diagnosis of ICD-9 code 850.0 according to one embodiment of the invention.

FIG. 14B is a flow diagram of a process for validating a specific diagnosis code, ICD-9 code 850.0, according to one embodiment of the invention. ICD-9 code 850.0 is defined as "concussion with no loss of consciousness." In step 200, receipt of this specific ICD-9 code prompts display of a question as to whether there was head trauma. If the response to the question is YES, a question is displayed in step 202 as to whether there was loss of consciousness. If the answer is YES, the entered ICD-9 code is verified in step 204. If the response to either the question of head trauma or loss of consciousness is negative, the ICD-9 code is not verified, as reflected by steps 206 and 208. In other words, in the absence of head trauma and/or loss of consciousness, ICD-9 diagnosis code 850.0 is deemed not valid.

History Based Filters

According to one embodiment of the invention, a plurality of filters are provided under a historical category which validate procedures based on analysis of historical data. In this regard, the computerized medical care system is configured to maintain the history of diagnoses and services that are rendered on a patent-by-patient basis in the historical database, as well as information on procedures and/or services rendered historically for each type of diagnoses.

Figure 15:
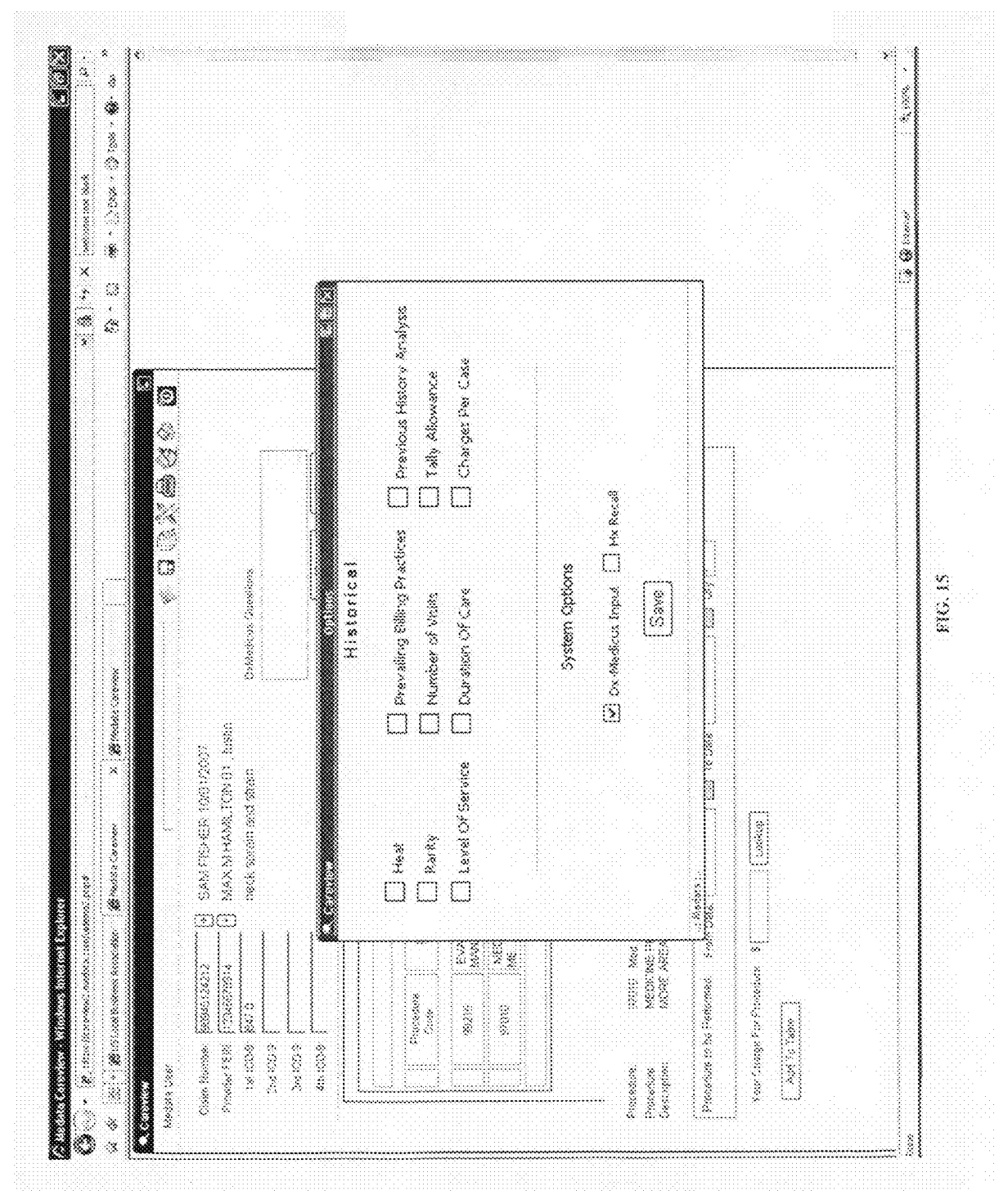

FIG. 15 is a screen capture of a graphical user interface listing various history based filters that may be enabled by a user according to one embodiment of the invention. Such history based filters include, but are not limited to a heat filter, rarity filter, level of service filter, prevailing billing practices filter, number of visits filter, duration of care filter, previous history analysis filter, TAL allowance filter, and charges per case filter.

Figure 16:
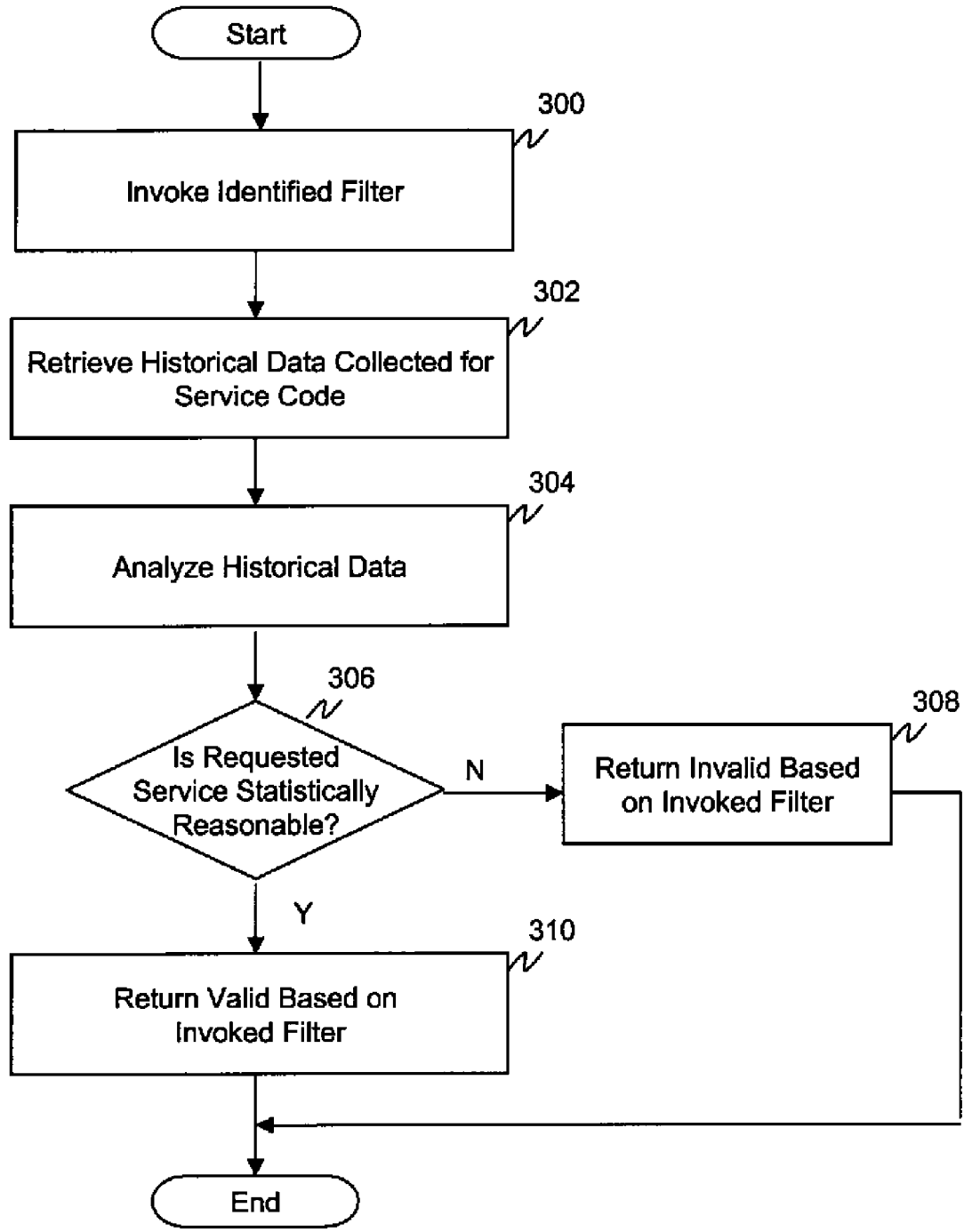
FIG. 16 is a generalized flow diagram for applying at least some history based filters according to one embodiment of the invention.

FIG. 16 is a generalized flow diagram of step 88 (FIG. 12) for applying at least some of the history based filters according to one embodiment of the invention.

In this regard, a specific historical filter that has been enabled is invoked in step 300 by the engine.

In step 302, historical data collected for the service code and/or conditions in which the identified medical service were rendered are retrieved from the historical database.

In step 304, the historical data is analyzed based on the invoked historical filter. This analysis may include, for example, determining a percentile distribution of the service code or of the conditions in which the identified service was rendered.

Based on the analysis of the historical data, a determination is made in step 306 as to whether the requested medical service is statistically reasonable. In this regard, the system may be configured with a reasonableness threshold, which, according to one embodiment of the invention, is selected by an administrator of the system. The selected reasonableness threshold may identify, for example, a threshold percentage value.

In making the determination of whether the requested service is statistically reasonable, a determination is made as to whether the requested service or condition surrounding the rendering of the requested service satisfies the threshold percentage value according to the analyzed percentage distribution data.

If the requested service is deemed to be statistically reasonable, the filter returns a result indicating that the requested service may be validated in step 310. Otherwise, the filter returns a resulting indicating that the requested service may not be validated in step 308.

Heat

According to one embodiment of the invention, the heat filter utilizes historical data to determine the appropriate use of heat-based physical therapy modalities on soft tissue injuries.

Soft tissue injuries, by nature, normally resolve within six to eight weeks from the date of injury. During this time, the conditions are considered to be in an "acute" phase. Inflammation, and the associated findings, characterize the conditions during this period. Therefore, the therapeutic goal in this time frame is to ameliorate the inflammation that is associated with the conditions. If the conditions do not resolve within this period, and remain symptomatic, then the conditions are considered to have progressed to a more chronic phase. The therapeutic goal of the chronic phase is to recondition and rehabilitate the patient to recover lost functions which can be responsible for the continued symptoms, and the failure to achieve full recovery.

The continued usage of these acute type therapies into the period when these injuries are chronic would afford this patient no therapeutic benefit. For example, for a patient that was injured on Feb. 1, 2008, physical therapy modalities (procedures 97010, 97012, 97014, etc.) would probably be of benefit if delivered prior to Mar. 15, 2008. Any of these modalities delivered after Mar. 15, 2008, are usually inappropriate if the patient's condition has moved to a more chronic phase. Thus, if the services being requested are being rendered subsequent to Mar. 15, 2008, the system is configured to generate and transmit a letter asking the provider to submit information which would support the medical necessity for care that is normally unnecessary in that time frame.

Figure 17:
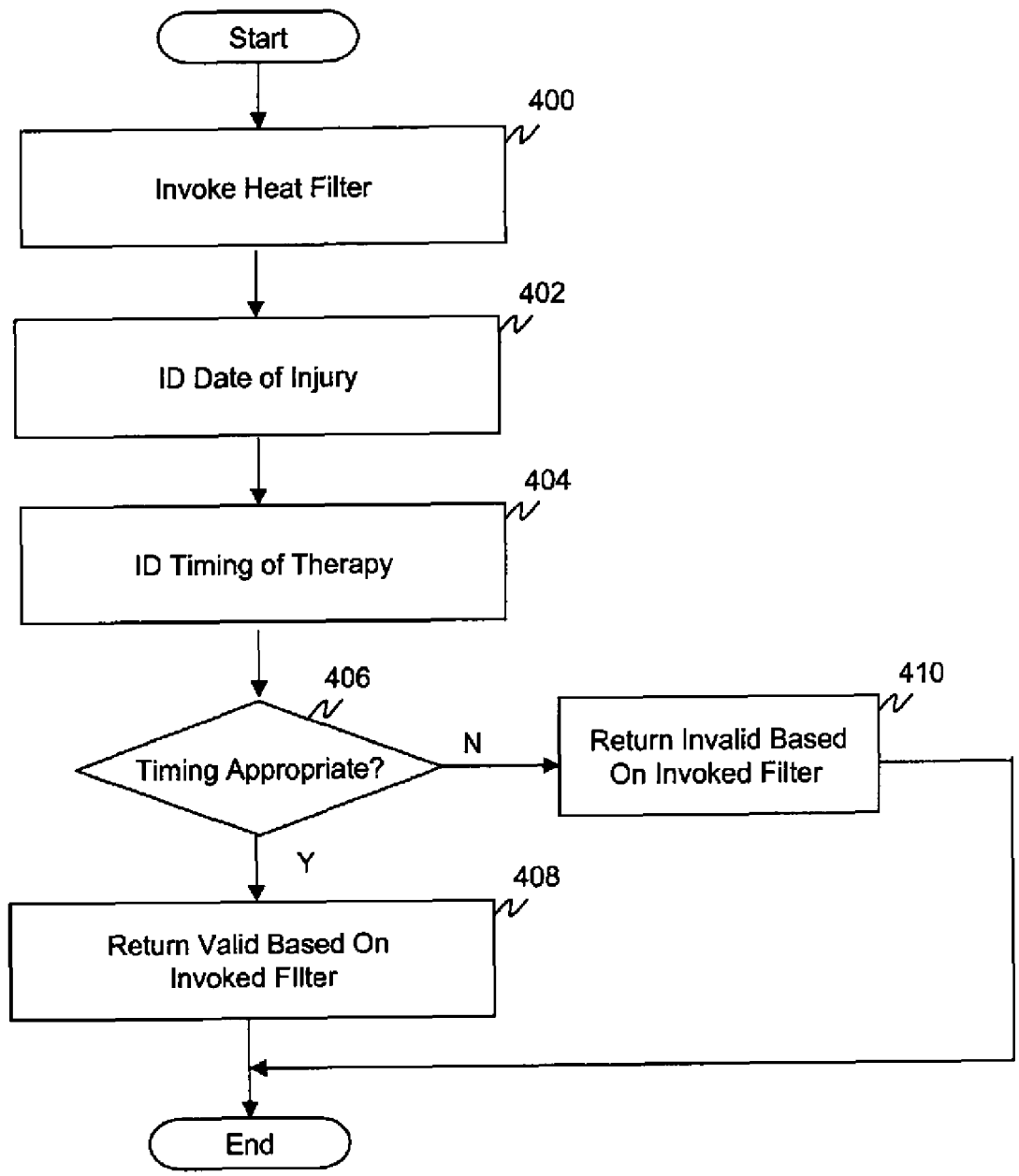
FIG. 17 is a flow diagram for applying a heat filter according to one embodiment of the invention.

FIG. 17 is a flow diagram of step 88 (FIG. 12) for applying a heat filter according to one embodiment of the invention. In step 400, the heat filter is invoked by the engine.

In step 402, the filter identifies a date of injury for which the heat-based physical therapy modality would be applied. This information may be provided by the medical service provider, for example, when entering the service code for the requested medical service.

In step 404, the timing of the heat-based physical therapy is identified.

In step 406, a determination is made as to whether the timing is appropriate. In this regard, the filter may compute a number of days from the date of the injury to the timing of the therapy, compare the number of days to a threshold number of days, and determine that the therapy is appropriate if the calculated number of days is within the threshold. The threshold number of days may be determined, for example, based on medical guidelines enabled for the system.

If the medical service is deemed to be appropriate, the filter returns a result indicating that the requested service may be validated in step 408. Otherwise, the filter returns a resulting indicating that the requested service may not be validated in step 410.

Rarity

Rarity is another filter which utilizes a database for determining the relatedness of a CPT code to the ICD-9 code. According to one embodiment, a rarity database which may form part of the database 140 is derived from over 700 million provider charges throughout the United States. The analysis of these charges determines the ratio between the number of times a specific procedure is performed for a specific ICD-9 diagnosis, as compared to all other procedures performed by all other providers billing for the same diagnosis.

Clients who utilize the rarity filter are able to determine a rarity ratio, that is, a threshold, that defines whether or not a CPT code is deemed rare for the submitted ICD-9. Although the ratio is statistically valid, it should not be applied arbitrarily. Therefore, when a proposed treatment is requested and falls outside the ratio, the provider is given every opportunity to justify the medical necessity for performing the procedure, in spite of the fact it is rarely performed for that diagnosis.

For example, in indemnity cases, CPT code 97010 (Hot/Cold Packs) accounts for one out of every ten procedures performed for ICD-9 code 847.2 (Lumbar Sprain/Strain) according to the data in the rarity database. The ratio for this procedure is one out of every ten. Therefore, it should not be considered rarely performed. On the other hand, analysis of the rarity database may indicate that CPT code 63030 (Lumbar Laminectomy) for ICD-9 code 847.2 (Lumbar Sprain/Strain) occurred only six times in 2,000,000 claims. This procedure is should therefore deemed to be rare.

Figure 18:
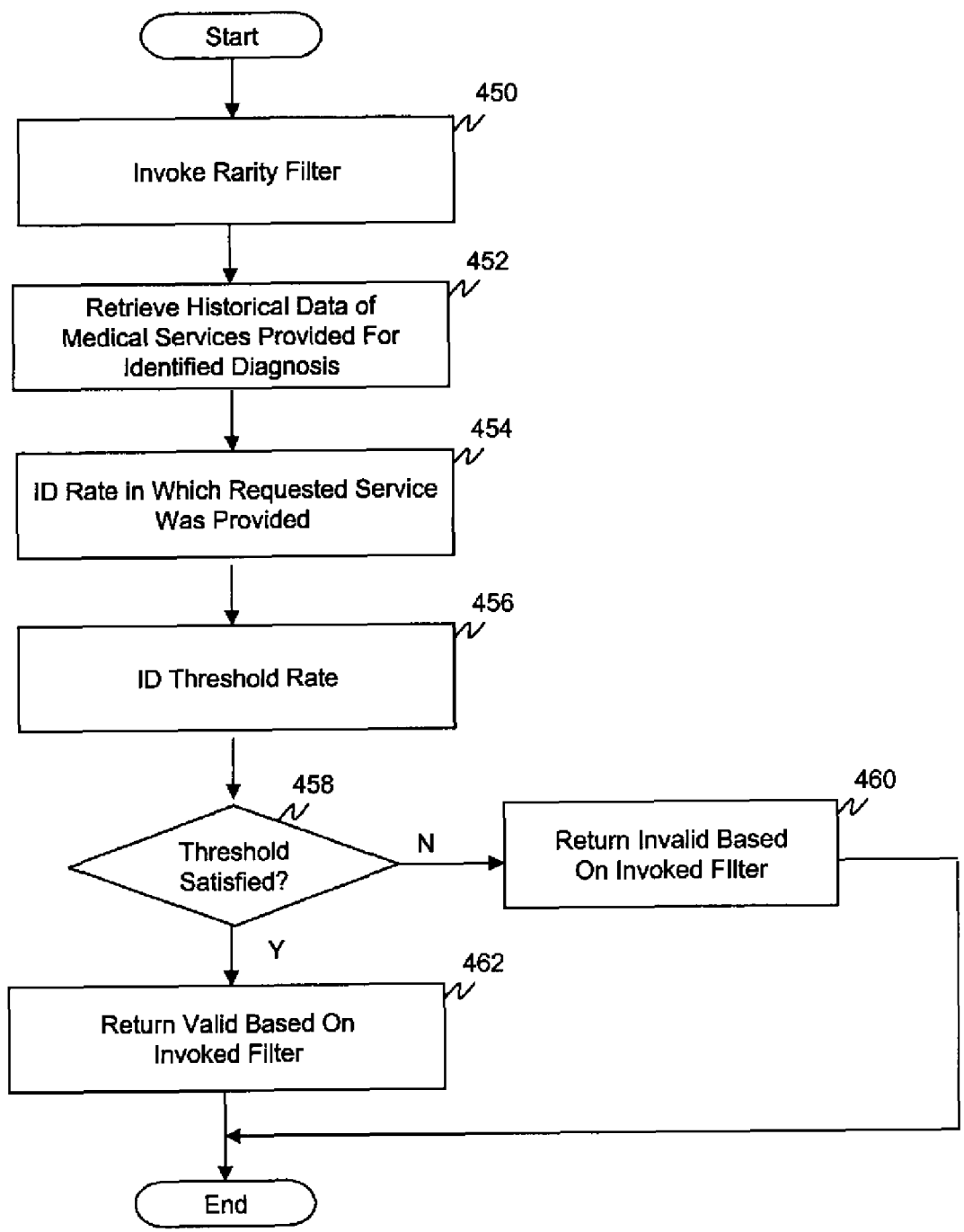
FIG. 18 is a flow diagram for applying a rarity filter according to one embodiment of the invention.

FIG. 18 is a flow diagram of step 88 (FIG. 12) for applying a rarity filter according to one embodiment of the invention. In this regard, in step 450, the rarity filter is invoked by the engine.

In step 452, the filter retrieves historical data from the rarity database of medical services provided for the identified diagnosis code.

In step 454, the filter analyzes the historical data to identify a rate in which the requested medical service was provided for the identified diagnosis code.

In step 456, a threshold rate is identified. In this regard, a system administrator may set a reasonable threshold rate that should be met if a procedure is not to be deemed to be rare.

In step 458, the filter determines if the threshold is satisfied by comparing the identified rate for the requested medical service against the threshold rate.

If the threshold is satisfied, the filter returns a result indicating that the requested service may be validated in step 462. Otherwise, the filter returns a resulting indicating that the requested service may not be validated in step 460.

Level of Service

Services necessary to satisfy the patient's needs are generally not constant but variable. For example, the Current Procedural Terminology (CPT) defines the Evaluation & Management procedures as follows:

| CODE | Description |
|---|---|
| | NEW PATIENT |
| 99201 | Office or other outpatient visit for the evaluation and management of a new patient, which requires these 3 key components<br>    A problem focused history<br>    A problem focused examination<br>    Straightforward medical decision making<br>Counseling and/or coordination of care with other providers or agencies are provided consistent with the nature of the problem(s) and the patient's and/or family's needs.<br>Usually, the presenting problem(s) are self limited or minor. Physicians typically spend 10 minutes face-to-face with the patient and/or family. |
| 99202 | Office or other outpatient visit for the evaluation and management of a new patient, which requires these 3 key components<br>    An expanded problem focused history<br>    An expanded problem focused examination<br>    Straightforward medical decision making<br>Counseling and/or coordination of care with other providers or agencies are provided consistent with the nature of the problem(s) and the patient's and/or family's needs.<br>Usually, the presenting problem(s) are self limited or minor. Physicians typically spend 20 minutes face-to-face with the patient and/or family. |
| 99203 | Office or other outpatient visit for the evaluation and management of a new patient, which requires these 3 key components<br>    A detailed history<br>    A detailed examination<br>    Medical decision making of low complexity<br>Counseling and/or coordination of care with other providers or agencies are provided consistent with the nature of the problem(s) and the patient's and/or family's needs.<br>Usually, the presenting problem(s) are self limited or minor. Physicians typically spend 30 minutes face-to-face with the patient and/or family. |
| 99204 | Office or other outpatient visit for the evaluation and management of a new patient, which requires these 3 key components<br>    A comprehensive history<br>    A comprehensive examination<br>    Medical decision making of moderate complexity<br>Counseling and/or coordination of care with other providers or agencies are provided consistent with the nature of the problem(s) and the patient's and/or |

-continued

| CODE | Description |
|---|---|
| | family's needs.<br>Usually, the presenting problem(s) are self limited or minor. Physicians typically spend 45 minutes face-to-face with the patient and/or family. |
| 99205 | Office or other outpatient visit for the evaluation and management of a new patient, which requires these 3 key components<br>    A comprehensive history<br>    A comprehensive examination<br>    Medical decision making of high complexity<br>Counseling and/or coordination of care with other providers or agencies are provided consistent with the nature of the problem(s) and the patient's and/or family's needs.<br>Usually, the presenting problem(s) are self limited or minor. Physicians typically spend 60 minutes face-to-face with the patient and/or family. |
| | ESTABLISHED PATIENT |
| 99211 | Office or other outpatient visit for the evaluation and management of an established patient, that may not require the presence of a physician. Usually, the presenting problem(s) are minimal. Typically, 6 minutes are spent performing or supervising these services. |
| 99212 | Office or other outpatient visit for the evaluation and management of an established patient, which requires at least 2 of these 3 key components<br>    An problem focused history;<br>    An problem focused examination;<br>    Straightforward medical decision making.<br>Counseling and/or coordination of care with other providers or agencies are provided consistent with the nature of the problem(s) and the patient's and/or family's needs.<br>Usually, the presenting problem(s) are self limited or minor. Physicians typically spend 10 minutes face-to-face with the patient and/or family. |
| 99213 | Office or other outpatient visit for the evaluation and management of a new patient, which requires at least 2 of these 3 key components<br>    An expanded problem focused history;<br>    An expanded problem focused examination;<br>    Medical decision making of low complexity.<br>Counseling and/or coordination of care with other providers or agencies are provided consistent with the nature of the problem(s) and the patient's and/or family's needs.<br>Usually, the presenting problem(s) are self limited or minor. Physicians typically spend 15 minutes face-to-face with the patient and/or family. |
| 99214 | Office or other outpatient visit for the evaluation and management of a new patient, which requires at least 2 of these 3 key components<br>    A detailed history<br>    A detailed examination<br>    Medical decision making of moderate complexity<br>Counseling and/or coordination of care with other providers or agencies are provided consistent with the nature of the problem(s) and the patient's and/or family's needs.<br>Usually, the presenting problem(s) are self limited or minor. Physicians typically spend 25 minutes face-to-face with the patient and/or family. |
| 99215 | Office or other outpatient visit for the evaluation and management of a new patient, which requires at least 2 of these 3 key components<br>    A comprehensive history<br>    A comprehensive examination<br>    Medical decision making of high complexity<br>Counseling and/or coordination of care with other providers or agencies are provided consistent with the nature of the problem(s) and the patient's and/or family's needs.<br>Usually, the presenting problem(s) are self limited or minor. Physicians typically spend 40 minutes face-to-face with the patient and/or family. |

According to one embodiment of the invention, billings from the historical database are reviewed to determine the appropriate level of service (LOS) for each of the International Classification of Disease—Revision 9 (ICD-9) codes. In this regard, based on the analysis of the bills, a determination is made as to the level of service that is most frequently used for each of the diagnoses. For example, review of the historical data may indicate that patients with sprains of the neck most frequently use a level equal to, or less than, 99202 for initial visits, and 99212 for subsequent visits. Therefore, any time a provider makes a request for a level of service in excess of those codes for this diagnosis, the system automatically generates a request for additional information that medically justifies the greater level of service being requested.

Figure 19:
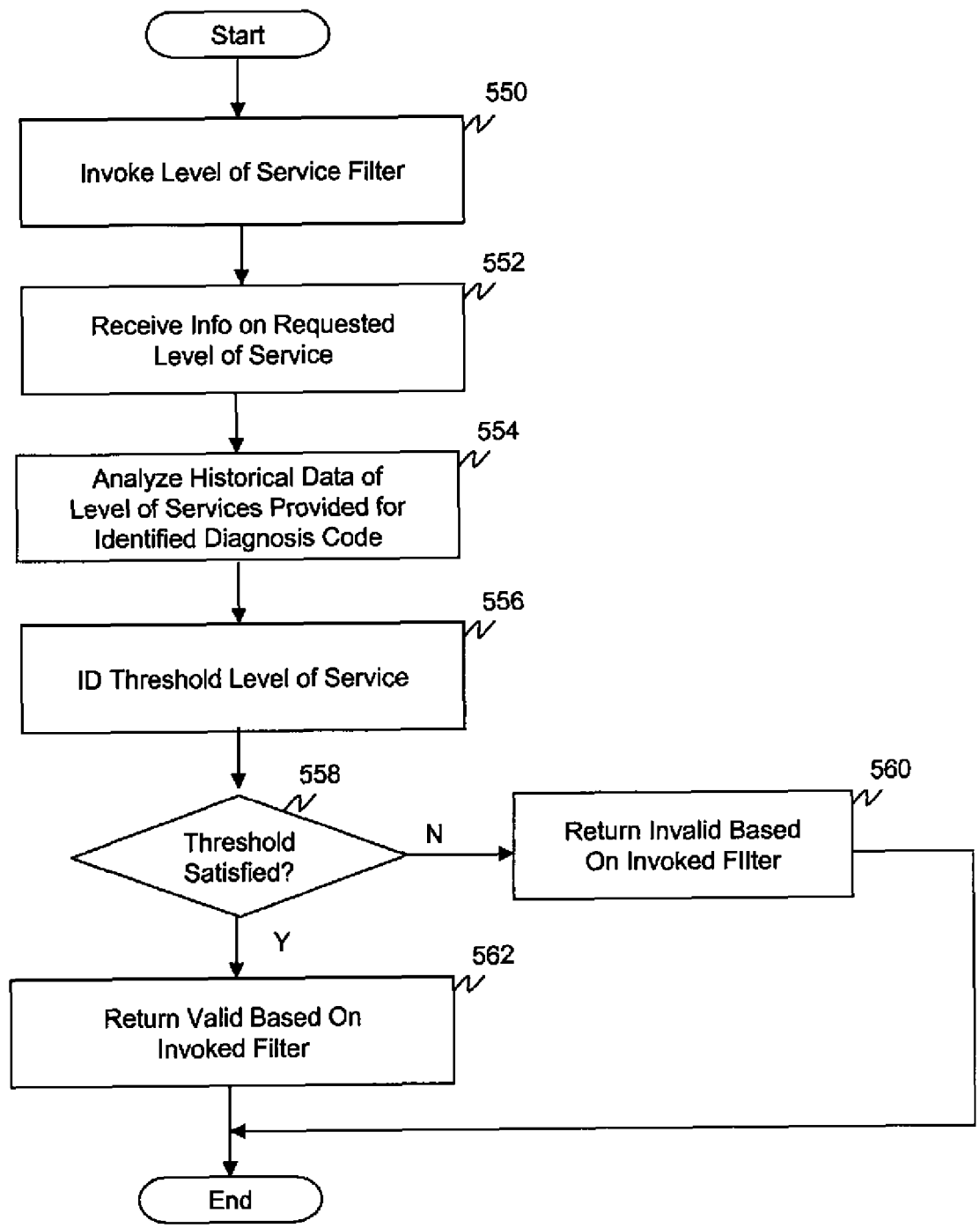
FIG. 19 is a flow diagram for applying a level of service filter according to one embodiment of the invention.

FIG. 19 is a flow diagram of step 88 (FIG. 12) for applying a level of service filter according to one embodiment of the invention. In this regard, in step 550, the level of service filter is invoked by the engine.

In step 552, the filter identifies a level of service associated with the identified service code.

In step 554, the filter retrieves and analyzes historical data of previous level of services provided for the identified diagnosis code. For example, the historical data may provide a percentage distribution for the different levels of services for the identified diagnosis code.

In step 556, the filter identifies a threshold level of service based on the analyzed historical data. For example, the filter may identify a level of service that has historically been rendered 90% of the time in which the particular diagnosis was made.

In step 558, a determination is made as to whether the threshold has been satisfied. That is, the filter determines whether the identified level of service is at or below the threshold level of service. According to one embodiment of the invention, the level of services increase with an increase in the associated service code. Thus, a level of service having code "99201" is deemed to be lower than a level of service having code "99202."

If the threshold is satisfied, the filter returns a result indicating that the requested service may be validated in step 562. Otherwise, the filter returns a resulting indicating that the requested service may not be validated in step 560.

Prevailing Billing Guidelines

According to one embodiment of the invention, analysis of historic medical provider billings yields information regarding how providers bill under normal circumstances. Prevailing billing guidelines may be derived from such analysis. The billing guidelines may cover a variety of different billing circumstances. Exemplary billing guidelines include:

a. The prevailing billing guideline for assistant surgeon fees is 20% of the surgeon's fee.

b. The prevailing billing guideline for surgeons performing several procedures at the same time, during the same session, is to charge the full amount for the primary procedure and charge 50% for all subsequent procedures performed during the same session.

c. Another prevailing billing guideline for certain surgery procedures is to include related services for the same diagnosis under the initial surgical procedure. This finding is important for deriving information about bundling and unbundling.

d. The charge for an examination of a patient is included in the charge for the major surgical procedure performed on the same day.

e. The charge for the major surgical procedure includes the services rendered subsequently for the condition for which the surgery was performed. This is referred to in peer review departments as the Follow Up Day (FUD) rule.

f. The charge for an initial/subsequent visit for a patient receiving physical therapy care is included in the value of the charges for the physical therapy session.

g. All radiology procedures contain inherent restrictions regarding the number of views taken. For example, a complete lumbar spine examination requires at least 4 views. A provider performing 3 views for a complete lumbar study is short 1 view and should be paid for a limited study.

h. The prevailing billing guideline for automated pathological procedures using computerized Sequential Multi-channel Analysis (SMA) have a single charge for the procedures. Too often, providers will charge as if these procedures were manually performed separately. This latter practice is not prevailing and probably hinges upon fraud.

Figure 20:
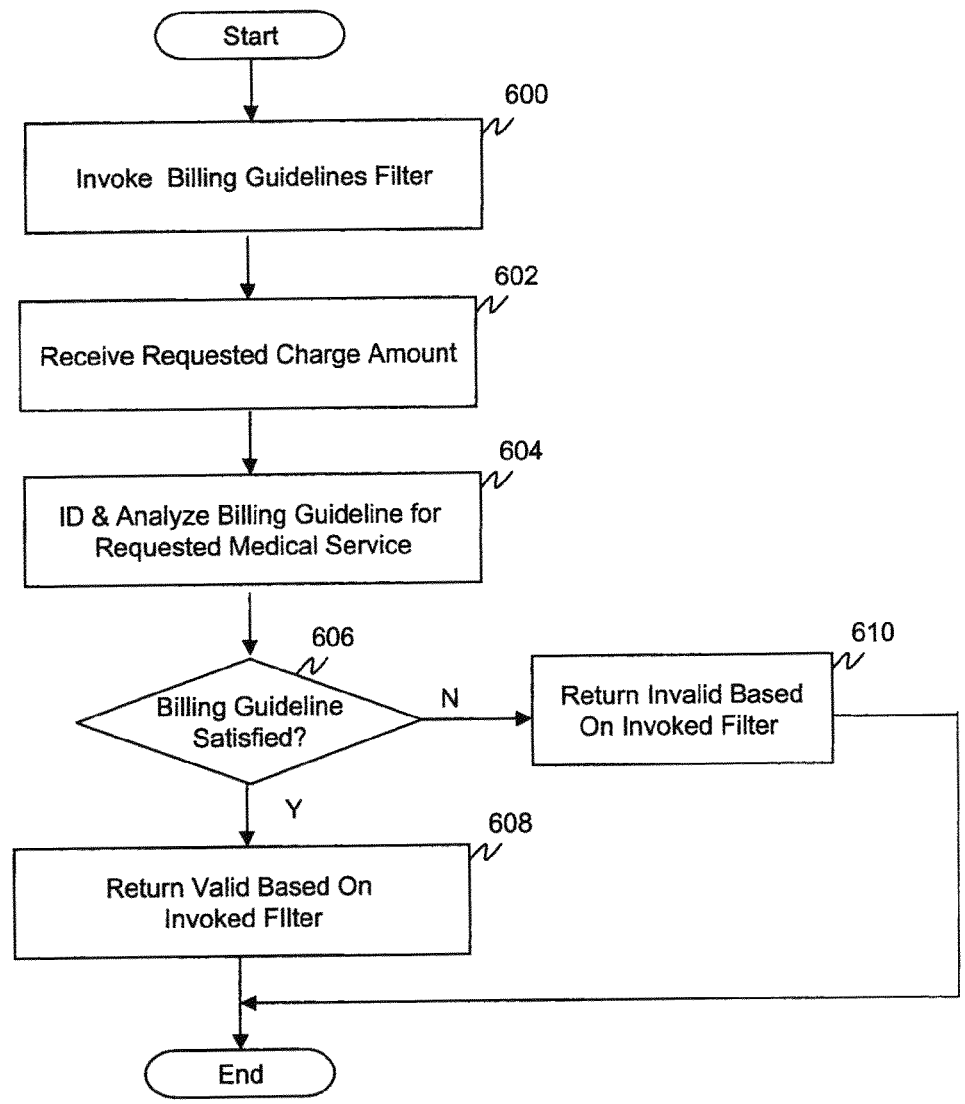
FIG. 20 is a flow diagram for applying a billing guidelines filter according to one embodiment of the invention.

FIG. 20 is a flow diagram of step 88 (FIG. 12) for applying a billing guidelines filter according to one embodiment of the invention. In this regard, in step 600, the billing guidelines filter is invoked by the engine.

In step 602, the filter receives a requested charge amount. For example, the amount may be entered by the medical service provider when entering the service code for the requested medical service.

In step 604, the filter identifies and analyzes the billing guideline for the requested medical service.

In step 606, a determination is made as to whether the billing guideline is satisfied. If the answer is YES, the filter returns a result indicating that the requested service may be validated in step 608. Otherwise, the filter returns a resulting indicating that the requested service may not be validated in step 610.

Number of Visits

According to one embodiment of the invention, the system includes various utilization filters 138 including a number of visits filter. This particular filter evaluates the percentile distribution of the number of visits claimants have been seen for various ICD-9 codes. For example, the following chart will distribute the number of visits seen for ICD-9 code 847.0 in approximately 200,000 claims:

| Percentile | 50th | 55th | 60th | 65th | 70th | 75th | 80th | 85th | 90th | 95th |
|---|---|---|---|---|---|---|---|---|---|---|
| Visits | 4 | 5 | 6 | 7 | 8 | 10 | 15 | 16 | 18 | 35 |

The client can select the percentile which they elect to use as being "the reasonable" value. The system stores the above information, plus the values for the 99$^{th}$ percentile as well. If the client selects the 80$^{th}$ percentile as being a reasonable number of visits, as based upon the analyzed history, then 15 visits is considered reasonable. Visits in excess of 15 would require some additional explanation from the provider indicating the medical necessity for the prolonged care.

Duration of Care

Another utilization filter 138 according to one embodiment of the invention is a duration of care filter. This particular filter evaluates the percentile distribution of duration of care for claimants who have been seen for various ICD-9 codes. For example, the following chart will distribute the duration of care for ICD-9 code 847.0 in approximately 2,000,000 claims:

As with the number of visits filter, the client can select the percentile which they elect to use as being "the reasonable" value. The system stores the above information, plus the values for the 99$^{th}$ percentile as well. If the client selects the 80$^{th}$ percentile as being a reasonable duration of care, as based upon the analyzed history, then 109 days would be considered reasonable. Duration of care exceeding 109 days would require some additional explanation from the provider indicating the medical necessity for the prolonged care.

Figure 21:
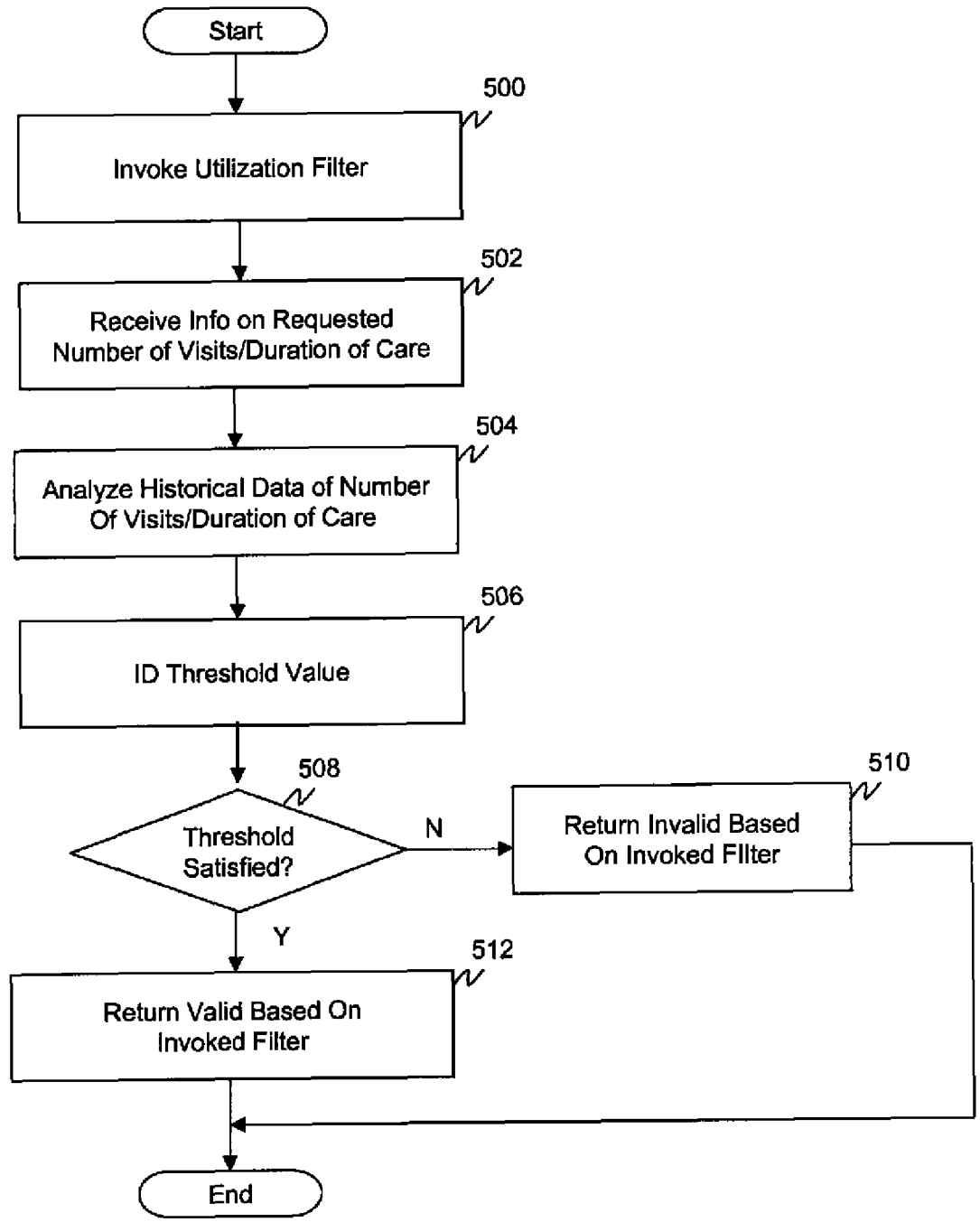
FIG. 21 is a flow diagram for applying a utilization filter according to one embodiment of the invention.

FIG. 21 is a flow diagram of step 88 (FIG. 12) for applying a utilization filter according to one embodiment of the invention. In this regard, in step 500, the utilization filter is invoked by the engine.

In step 502, the filter receives information on a requested number of visits or duration of care for the identified service code. For example, this information may be entered by the medical service provider when entering the service code for the requested medical service.

In step 504, the filter retrieves and analyzes historical data of previous number of visits or duration of care provided for the identified diagnosis code. This analysis may include, for example, determining a percentile distribution of the number of visits or duration of care for the identified diagnosis code.

In step 506, a threshold percentile value is identified. According to one embodiment of the invention, the threshold percentile value may be set by a system administrator. Based on this threshold percentile value, a threshold number of visits or duration of care may be identified from the historical data.

In step 508, a determination is made as to whether the threshold value has been satisfied. In this regard, the filter determines whether the indicated number of visits or duration of care is not more than the threshold number of visits or duration of care.

If the answer is YES, the filter returns a result indicating that the requested service may be validated in step 512. Otherwise, the filter returns a resulting indicating that the requested service may not be validated in step 510.

Previous History Analysis

According to one embodiment of the invention, the system also includes a patient history filter which analyzes the patient's previous history in order to determine the appropriateness and validity of the care. For example, a patient with a previous amputation of the right thumb would not be a good candidate for an amputation of the right thumb. Furthermore, a patient who already has had an appendectomy would not need another.

According to one embodiment of the invention, the system maintains a history of all previous care that has been rendered to a specific patient for the current condition. The system further collects information on what has worked successfully

| Percentile | 50th | 55th | 60th | 65th | 70th | 75th | 80th | 85th | 90th | 95th |
|---|---|---|---|---|---|---|---|---|---|---|
| Duration | 32 | 43 | 56 | 68 | 8 | 80 | 93 | 109 | 132 | 253 | for previous patients and what has not. This helps to prevent treating a patient with a modality that has no therapeutic benefit.

Figure 22:
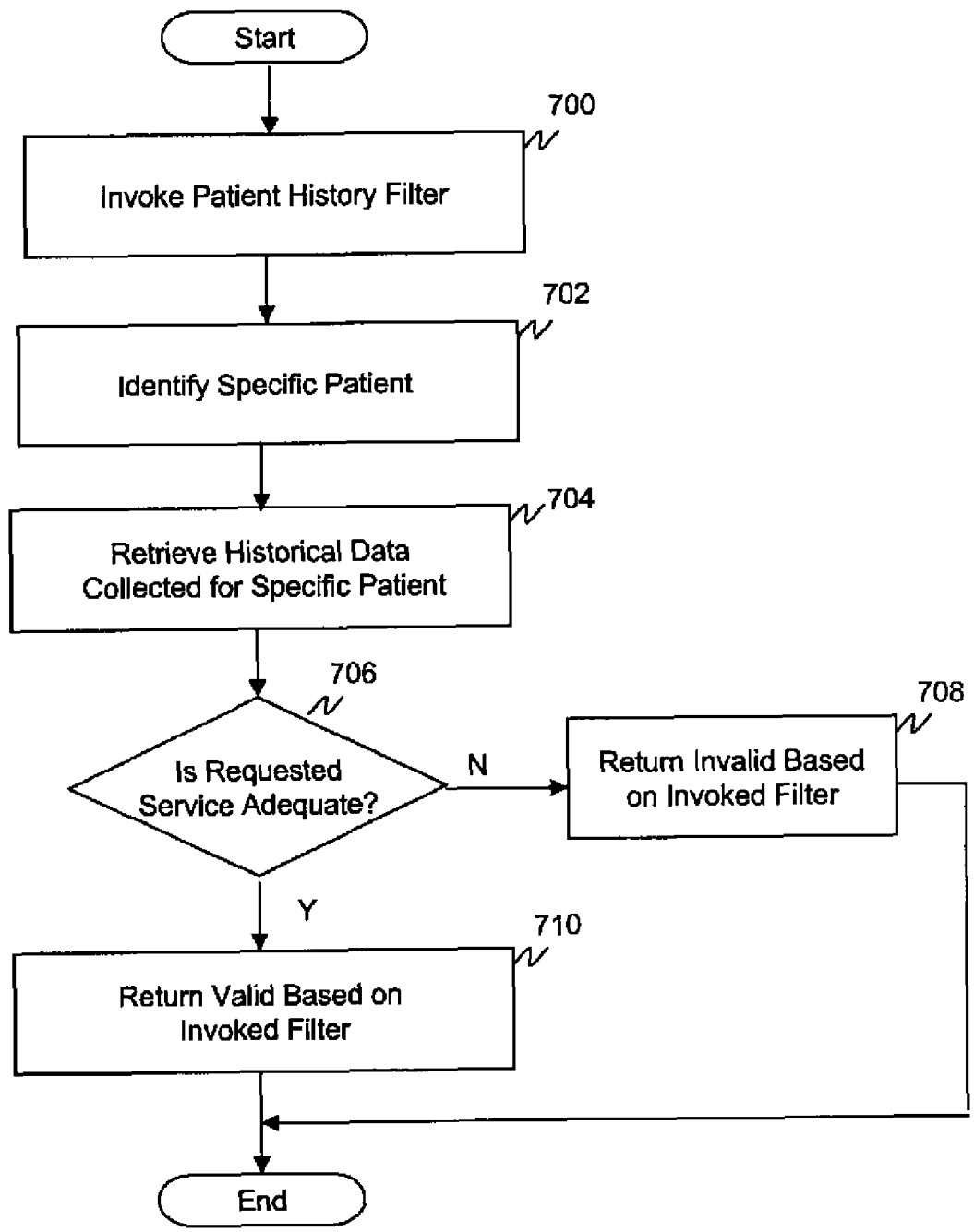
FIG. 22 is a flow diagram for applying a patient history filter according to one embodiment of the invention.

FIG. 22 is a flow diagram of step 88 (FIG. 12) for applying a patient history filter according to one embodiment of the invention. In this regard, in step 700, the patient history filter is invoked by the engine.

In step 702, the filter identifies a specific patient for which pre-approval is being requested.

In step 704, the filter retrieves and analyzes historical data collected for the specific patient. In this regard, the filter may retrieve and analyze data on previous medical services provided for the specific medical condition that has currently been diagnosed.

In step 706, a determination is made as to whether the requested medical service is adequate 706. In this regard, the filter may determine whether a requested medical service is one that should not be repeated twice on a particular body part, within a certain period of time, or the like.

If the requested medical service is adequate, the filter returns a result indicating that the requested service may be validated in step 710. Otherwise, the filter returns a resulting indicating that the requested service may not be validated in step 708.

TAL Allowance

According to one embodiment of the invention, a TAL filter is used to determine the reasonableness of a procedure or service when there is not a value already designated by a fee schedule, or a contracted rate. According to one embodiment, unlike other "usual & customary" charges databases, the charges used by the TAL filter are derived from actual provider charges. In other words, every specific value in the TAL database may be supported by information that was used to create that value. The value may be traced to a specific provider's charge for a procedure performed for a specific patient on a specific date on a specific billing. For example, one of the charges that may contribute to the value used by the TAL filter was performed by Dr. Jones on patient Smith on Oct. 22, 2006 on billings submitted to ABC Insurance Company on Nov. 30, 2006. This audit trail can help prove the validity of the reasonableness value of the procedure allowance.

Total Charges per Case

According to one embodiment of the invention, the system further includes a "Total Claim Charges" filter. This particular filter evaluates the percentile distribution of total claim cost for claimants who have been seen for various ICD-9 codes. For example, the following chart will distribute the total claim cost for ICD-9 code 847.0 in approximately 2,000,000 claims:

above data shows that 80% of 65,112 claims which share the ICD-9 code 847.0 had total charges of $4,849.90 or less and only 20% had charges in excess of this amount.

According to one embodiment, a system administrator may select the percentile that is deemed to be a reasonable value. If the system administrator selects the $80^{th}$ percentile as being a reasonable amount for total claim charges, as based upon the analyzed history, then a total claim charge of $5,846.00 would be considered reasonable for PI cases, while $4,849.90 would be considered reasonable for WC cases. Visits in excess of 15 would require some additional explanation from the provider indicating the medical necessity for the prolonged care.

Figure 23:
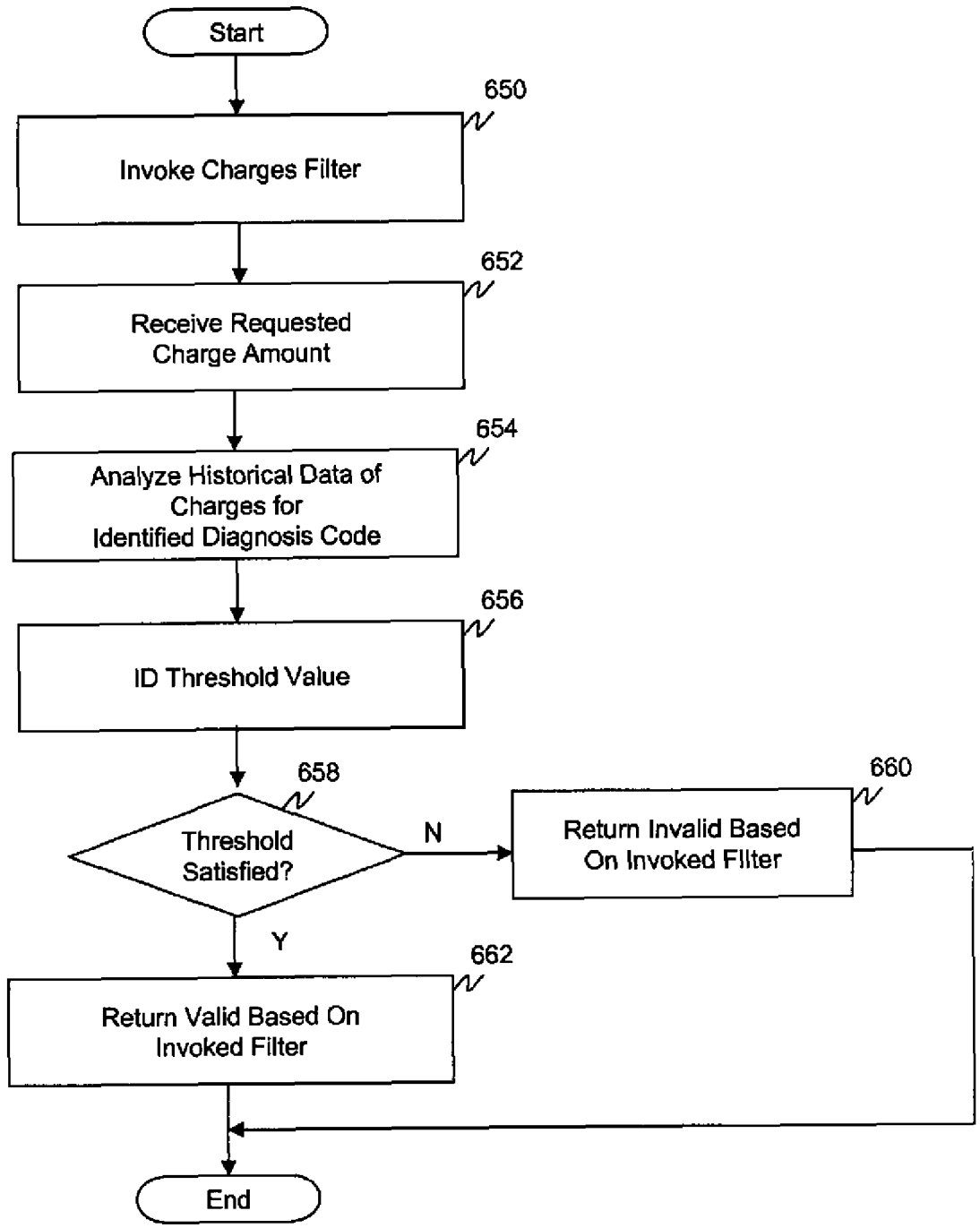
FIG. 23 is a flow diagram for applying a charges filter according to one embodiment of the invention.

FIG. 23 is a flow diagram of step 88 (FIG. 12) for applying a charges filter according to one embodiment of the invention. In this regard, in step 650, the charges filter is invoked by the engine.

In step 652, the filter receives a requested charge amount. For example, this information may be entered by the medical service provider when entering the service code for the requested medical service.

In step 654, the filter retrieves and analyzes historical data of charges made for the identified diagnosis code. This analysis may include, for example, determining a percentile distribution of the charges for the identified diagnosis code based on the historical data in the historical database.

In step 656, a threshold percentile value is identified. According to one embodiment of the invention, the threshold percentile value may be set by a system administrator. Based on this threshold percentile value, a threshold charge amount may be identified from the historical data.

In step 658, a determination is made as to whether the threshold value has been satisfied. In this regard, the filter determines whether the indicated charge is not more than the threshold charge amount.

If the answer is YES, the filter returns a result indicating that the requested service may be validated in step 662. Otherwise, the filter returns a resulting indicating that the requested service may not be validated in step 660.

State Workers' Compensation Filters

According to one embodiment, rules and allowance recommendations for all Workers' Compensation claims in all states of the United States may be selected for being applied to a pre-approval request. FIG. 23 is an exemplary screen capture of a graphical user interface for selecting the various states. This screen allows for the selection of the rules of the state and allowances within the state to be enabled. For states without fee schedules, the TAL filter may be enabled for paying a reasonable allowance for care rendered. The CPT with its many rules can optionally be turned on or off by clicking on or off the option prompt.

| Percentile | 50th | 60th | 70th | 80th | 90th | 95th |
|---|---|---|---|---|---|---|
| PI Total Charges | 2,230.00 | 2,950.00 | 3,980.00 | 5,846.00 | 9,630.00 | 14,697.38 |
| WC Total Charges | 1,045.24 | 1,630.38 | 2,666.37 | 4,849.90 | 12,229.89 | 27,927.59 |

Figure 24:
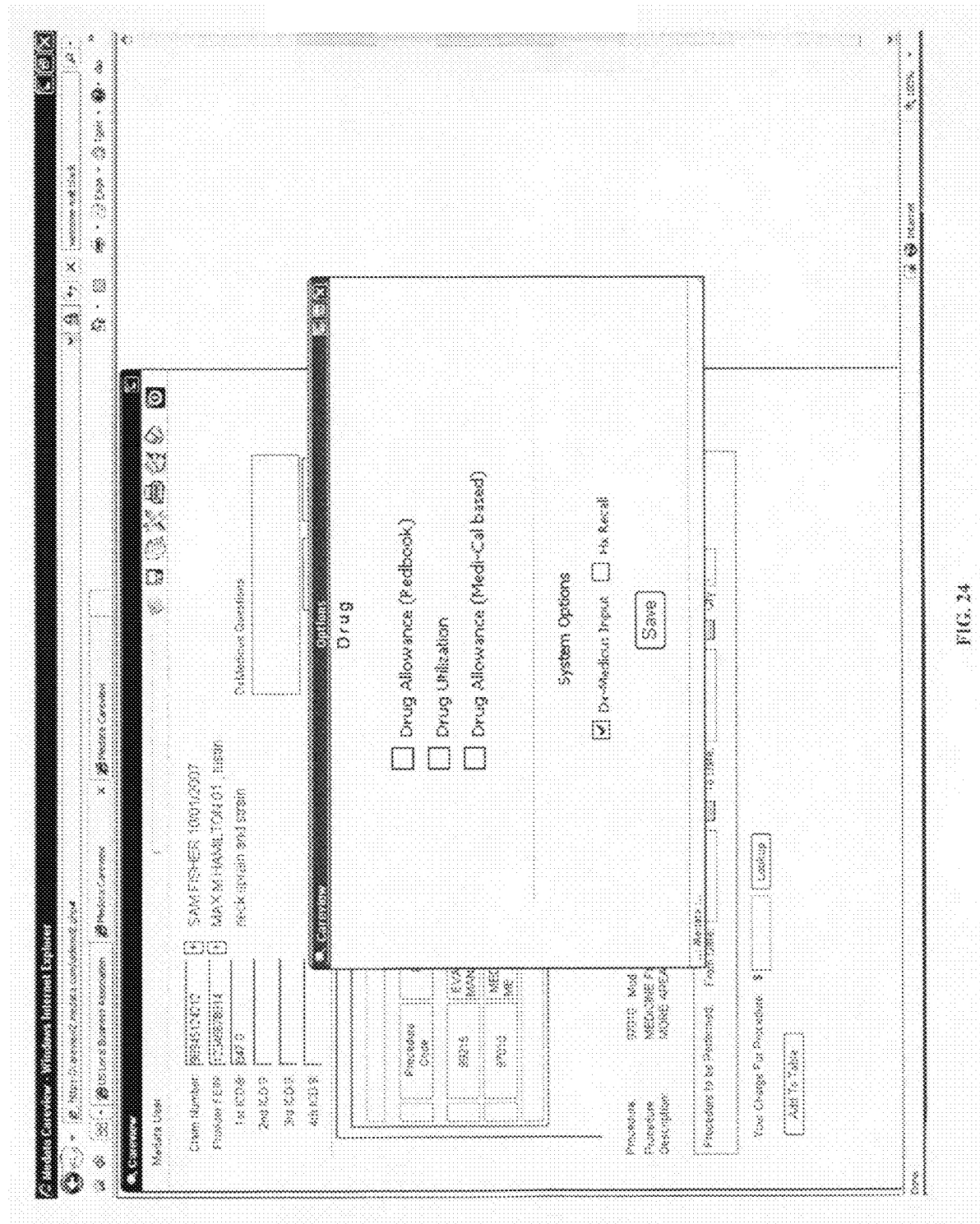
FIG. 24 is an exemplary screen capture of a graphical user interface for enabling a particular drug allowance guide for dispensing medications according to one embodiment of the invention.

The system stores the above information, plus the values for the $55^{th}$, $65^{th}$, $75^{th}$ $85^{th}$ and $99^{th}$ percentiles as well. For Personal Injury (PI), the above data shows that 80% of 384,840 claims which share the ICD-9 code 847.0 had total charges of $5,846.00 or less and only 20% had charges in excess of this amount. For Workers' Compensation (WC), the Drug Screen Shots FIG. 24 is an exemplary screen capture of a graphical user interface for enabling a particular drug allowance guide for dispensing medications according to one embodiment of the invention. One consideration in prescribing medication to a patient is whether the medication has any therapeutic benefit for the patient's condition. Another consideration is what the cost of the medication would be to a third-party payer. Overcharging for dispensed medications, prescriptions and related medical appliances is not only bad business practice but uses important resources in an inefficient manner.

Each of the three options illustrated in FIG. 24, that is, Drug Allowance (Redbook), Drug Utilization, and Drug Allowance (MediCal) include a determination of the appropriate allowance for dispensing a medication and for providing information regarding any adverse drug interactions that may be experienced by the patient for the medications currently prescribed. This analysis will include an analysis being requested at the instant moment and drug interaction for the drugs currently being taken by the patient, which have been previously dispensed.

Claim Environment Screen Shots

Figure 25:
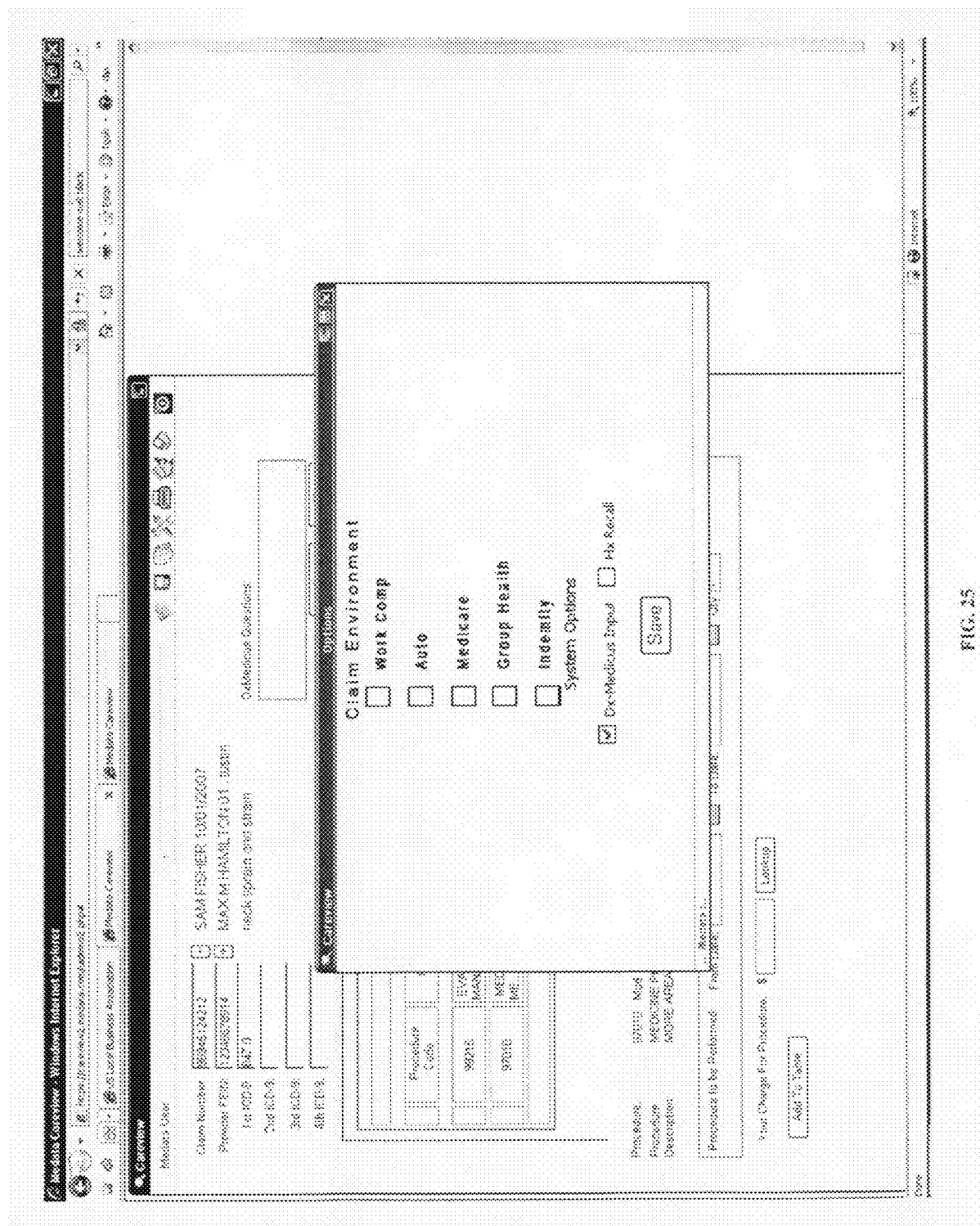
FIG. 25 is an exemplary screen capture of a graphical user interface for selecting one or more of different types of claims that may be processed according to one embodiment of the invention.

FIG. 25 is an exemplary screen capture of a graphical user interface for selecting one or more of different types of claims that the system is to process. The rules, authorization considerations, treatment parameters and allowance reimbursement for each of the claim environments are different from each other. In this regard, the automated medical care system according to embodiments of the present invention stores in the database 140 the rules, authorization considerations and treatment parameters for each of the specific claim environments. For example, the system does not apply Medicare rules to workers' compensation cases and vice versa. Thus, when a Medicare claim type has been enabled, the various filters discussed above apply rules specific to Medicare claims.

Medical Screen Shots

Figure 26:
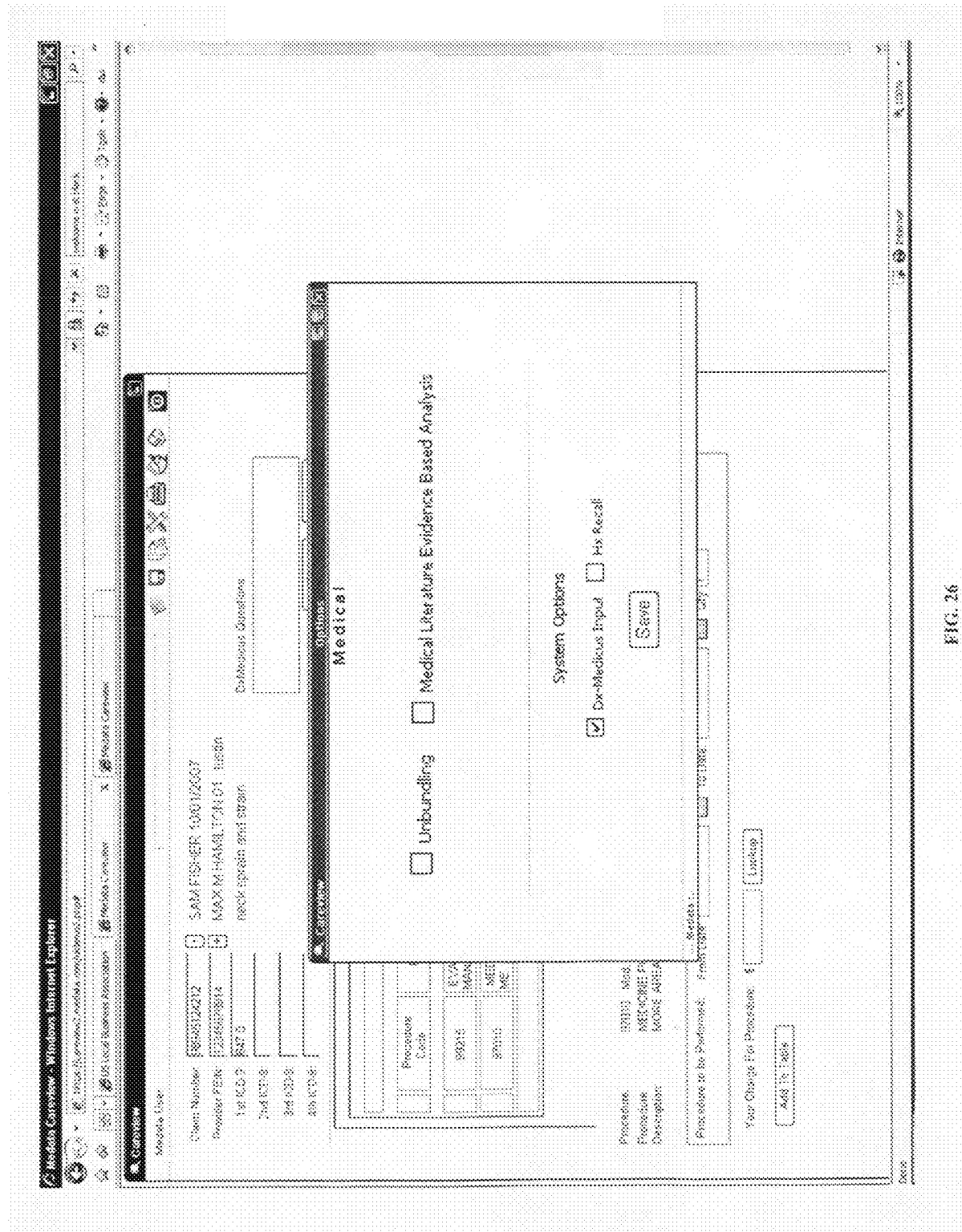
FIG. 26 is an exemplary screen capture of a graphical user interface for selecting an unbundling medical filter and/or a medical literature evidence based analysis according to one embodiment of the invention.

FIG. 26 is an exemplary screen capture of a graphical user interface for selecting an unbundling medical filter and/or a medical literature evidence based analysis according to one embodiment of the invention. There are a number of prevailing billing practices associated with the delivery of medical care in the United States. These practices are adhered to in order to improve the quality and efficiency of care delivered to patients. Unbundling refers to separating services that would normally be covered under a single procedure into its parts in order to increase charges for the service. The practice is abhorred by both medical peer review and medical authority. The automated medical care system includes information in its database which defines every instance of unbundling.

The Medical Literature Experience Based Analysis filter is based upon the world medical literature, which contains information regarding good medical care. The database 142 includes numerous articles in the literature and are configured to be drawn upon to notify the medical provider of information that is either of benefit or deleterious in the treatment of patients. This information is instantly available to be transmitted to any providers questioning the medical validity of the system decisions.

Miscellaneous Medical Rules Screen Shot

Figure 27:
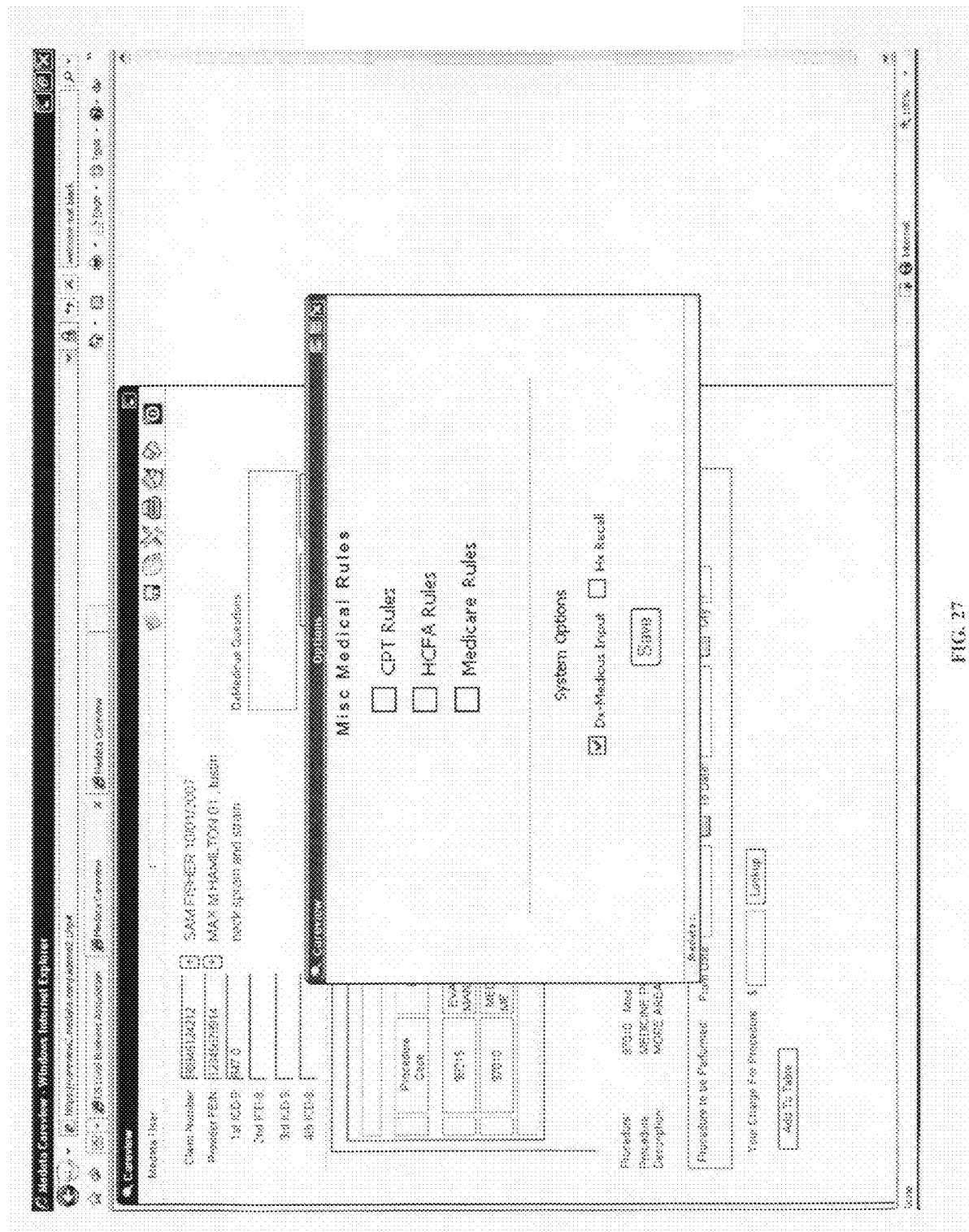
FIG. 27 is an exemplary screen capture of a graphical user interface for selecting miscellaneous medical rules to be enabled for applying those rules in the validating or invalidating of medical diagnoses and medical procedures according to one embodiment of the invention.

FIG. 27 is an exemplary screen capture of a graphical user interface for selecting miscellaneous medical rules to be enabled for applying those rules in the validating or invalidating of medical diagnoses and medical procedures according to one embodiment of the invention. In this regard, there are a number of sources of medical care guidelines used to determine appropriate medical care. These sources contain rules and treatment parameters that may be invoked in addition to any rules provided by the filters described above. For example, the American Medical Association publishes the Current Procedural Terminology Revision 4 (CPT-4) to define all of the treatments rendered by medical physicians in the United States. This document is updated on a yearly basis and is laden with the valuable medical guidelines. According to one embodiment, all of the guidelines found in the CPT-4 are found in the database 142 and are appropriately applied by the automated medical authorization system according to various embodiments of the present invention.

Health Care Financing Administration (HCFA) writes a number of rules governing the appropriate application of medical care. These rules are published periodically in the Federal Register. The rules of HCFA are also incorporated within the database and are appropriately applied when activated.

The Medicare Administration further produces documents which define the delivery of medical care to Medicare patients. The rules of the Medicare administration are found within the database and are also appropriately applied when activated.

According to one embodiment, each of the option categories mentioned above can be changed based upon current medical and organizational necessity. Further, as the management of medical care changes from time to time, option field categories can be changed to keep pace with current necessity.

Although exemplary embodiments of the present invention have been described, they should not be construed to limit the scope of the appended claims. Those skilled in the art will understand that various modifications may be made to the described embodiments and that numerous other configurations are capable of achieving this same result.

It is the applicant's intention to cover by claims all such uses of the invention and those changes and modifications which could be made to the embodiments of the invention herein chosen for the purpose of disclosure without departing from the spirit and scope of the invention.

What is claimed is:

1. In a computerized medical care system, a method for providing pre-approval for medical services and charges associated with the medical services, the method comprising:
   receiving by a server computer from a requesting device, a medical claim including a service code associated with a proposed medical service for a diagnosed condition for a patient prior to rendering the medical service by a medical provider, and a proposed charge for the medical service;
   identifying by the server computer one or more filters enabled for the computerized medical care system;
   applying by the server computer the identified one or more filters for the received medical claim, the identified filters accessing a historical database of patient records with historical data on medical procedures rendered to at least a plurality of other patients for the diagnosed condition, wherein the historical data includes data of past charges for the proposed medical service;
   determining by the server computer whether the proposed medical service is medically necessary for the diagnosed condition and whether the proposed charge is reasonable or unreasonable, based on at least the historical data, wherein the determining whether the proposed charge is reasonable or unreasonable includes comparing the proposed charge to a threshold value selected based on the historical data of past charges for the proposed medical service for determining that the proposed charge is presumptively unreasonable if the charge is above the threshold value, but reasonable if the proposed charge is at or below the threshold value;
   providing by the server computer based on the determination, feedback to the requesting device on whether the proposed medical service is medically necessary and reasonably charged prior to the rendering of the medical service by the medical provider, wherein if the proposed medical service is determined to be medically necessary and reasonably charged, the feedback includes pre-approval for the received medical claim for ensuring payment to the medical provider according to the proposed charge; and if the proposed medical service is determined to be medically unnecessary based on at least the historical data, prompting the medical provider by the server computer to submit information justifying the proposed service for reevaluating the proposed medical service; and if the proposed charge is determined to be unreasonable based on at least the historical data, determining by the server computer a reasonable amount that will be paid to the medical provider and informing the medical provider of the determined amount, the server computer further prompting the medical provider to submit information justifying the proposed charge for reevaluating the proposed charge.

2. The method of claim 1 further comprising:
displaying a question that should be considered in making the diagnosis of the condition;
prompting a user response to the displayed question;
receiving the user response to the displayed question;
comparing an expected response to the displayed question with the received user response; and
validating the diagnosis if the expected response matches the received user response.

3. The method of claim 1, wherein a plurality of the filters are applied one by one in sequence.

4. The method of claim 1 further comprising:
providing by the server computer a graphical user interface with a list of the one or more filters;
receiving a user selection of desired ones of the one or more filters; and
enabling each selected filter for determining whether the proposed medical service is medically necessary for the diagnosed condition, and whether the proposed charge is reasonable or unreasonable.

5. The method of claim 1, wherein the determining whether the proposed medical service is medically necessary includes:
analyzing by the server computer the historical data in the historical database on medical services rendered historically for the diagnosed condition and conditions for rendering the medical services;
identifying proposed conditions for rendering the proposed medical service;
identifying, based on the analyzed historical data, percentile distribution values for respectively the proposed medical service and the proposed conditions; and
determining that the proposed medical service is medically necessary if the identified percentile distribution values are at least equal to predetermined percentile distribution values selected by a user.

6. The method of claim 5 further comprising:
adding to the historical database information on the medical service proposed for the diagnosed condition.

7. The method of claim 5, wherein the conditions are selected from a group consisting of duration of care, number of visits, and the proposed charge for the medical service.

8. The method of claim 5, wherein the predetermined percentile distribution values are user customized.

9. The method of claim 1, wherein at least one of the one or more filters is a heat filter, and the determining of whether the proposed medical service is medically necessary based on the heat filter includes:

identifying a date of injury;
identifying a timing of the proposed medical service, wherein the proposed medical service is a heat-based therapy; and
determining that the medical service is medically necessary based on the timing of the heat-based therapy relative to the date of injury.

10. The method of claim 1, wherein at least one of the one or more filters is a rarity filter, and the determining of whether the proposed medical service is medically necessary based on the rarity filter includes:
retrieving by the server computer from the historical database the historical data of medical services historically provided for the diagnosed medical condition;
identifying a rate in which the proposed medical service was provided for the identified diagnosis based on the retrieved historical data;
identifying a threshold rate; and
determining that the proposed medical service is medically necessary based on a determination that the identified rate is equal or above the threshold rate.

11. The method of claim 10, wherein the threshold rate is user customized.

12. The method of claim 1, wherein at least one of the one or more filters is a utilization filter, and the determining of whether the proposed medical service is medically necessary based on the utilization filter includes:
receiving information on one of a number of visits and duration of care requested for rendering the proposed medical service;
analyzing the historical data in the historical database on one of a number of visits and durations of care provided historically for the diagnosed condition;
identifying one of a threshold number of visits and durations of care based on the analyzed data;
determining that the medical service is medically necessary based on a determination that one of the requested number of visits and duration of care is equal or below the identified threshold number.

13. The method of claim 1, wherein at least one of the one or more filters is a level of service filter, and the determining of whether the proposed medical service is medically necessary based on the level of service filter includes:
identifying a level of service associated with the proposed medical service;
analyzing the historical data in the historical database on levels of service provided historically for the diagnosed condition;
identifying a threshold level of service based on the analyzed data; and
determining that the medical service is medically necessary based on a determination that the identified level of service is equal or below the threshold level of service.

14. The method of claim 1, wherein at least one of the one or more filters is a billing guidelines filter, and the determining of whether the proposed charge is reasonable or unreasonable based on the billing guidelines filter includes:
identifying by the server computer a billing guideline associated with the proposed medical service; and
determining that the proposed charge is reasonable if the proposed charge complies with the identified billing guideline.

15. The method of claim 1, wherein at least one of the one or more filters is a charges filter, and the determining of whether the proposed charge is reasonable or unreasonable includes:

analyzing the historical data including total charges for the diagnosed condition;

identifying based on the analyzed historical data, a percentile distribution value for proposed total charges for the diagnosed condition; and determining that the proposed total charges is reasonable if the percentile distribution value for the proposed total charges is equal or below a predetermined percentile distribution value.

16. The method of claim 15, wherein the predetermined percentile distribution is user customized.

17. The method of claim 1, wherein the feedback is a letter generated in real time with the determining of whether the proposed medical service is medically necessary.

18. The method of claim 1, wherein the applying of at least one of the one or more filters includes:

identifying the patient for whom the medical service is proposed;

retrieving historical data of medical care provided to the patient; and determining based on the retrieved historical data for the patient that the proposed medical service is medically necessary for the patient if the proposed medical service is not inconsistent with prior medical services received by the patient.

19. The method of claim 1 further comprising:

identifying by the server computer a charge allowed for the proposed medical service;

comparing by the server computer the proposed charge and the charge allowed;

determining by the server computer that the proposed medical service is unreasonably charged if the proposed charge exceeds the charge allowed; and prompting by the server computer to submit information justifying the proposed charge for reevaluating the medical claim.

20. The method of claim 1, wherein the feedback provided by the server computer includes a prompt for prompting the medical provider to provide the information.

21. The method of claim 1, wherein the threshold value for determining whether a proposed charge is reasonable or unreasonable for a first user differs from the threshold value for determining whether a proposed charge is reasonable or unreasonable for a second user.

22. The method of claim 1, wherein the threshold value is a threshold dollar amount.

23. The method of claim 22, wherein the threshold value is associated with a percentile distribution value indicating a percent of the past charges in the historical database at or below the threshold dollar amount.

24. The method of claim 23, wherein the percentile distribution value is selected by a user for determining whether the proposed charge is reasonable or unreasonable.

25. The method of claim 24, wherein the percentile distribution value is selected by the user from a plurality of possible percentile distribution values stored in the historical database.

26. The method of claim 24, wherein the selected percentile distribution value is 80%.

27. The method of claim 24, wherein the percentile distribution value selected by a first user differs from the percentile distribution value selected by a second user.

28. The method of claim 1, wherein the service code is a medical diagnosis code.

29. The method of claim 28, wherein the service code is an international classification of diseases code.

30. The method of claim 1, wherein the one or more filters are medical procedure filters.

31. The method of claim 1, wherein the one or more filters implement rules provided by one or more medical organizations.

32. The method of claim 1, wherein the one or more filters are associated with specific geographic locations.

33. The method of claim 1, wherein the one or more filters apply a first set of rules based on a first type of medical claim, and a second set of rules based on a second type of medical claim.

34. A computerized medical care system for providing pre-approval for medical services and charges associated with the medical services, the system comprising:

a processor; and a memory operably coupled to the processor and storing program instructions therein, the processor being operable to execute the program instructions, the program instructions including:

receiving from a requesting device a medical claim including a service code associated with a proposed medical service for a diagnosed condition for a patient prior to rendering the medical service by a medical provider, and a proposed charge for the medical service;

identifying one or more filters enabled for the computerized medical care system;

applying the identified one or more filters for the received medical claim, the identified filters accessing a historical database of patient records with historical data on medical procedures rendered to at least a plurality of other patients for the diagnosed condition, wherein the historical data includes data of past charges for the proposed medical service;

determining whether the proposed medical service is medically necessary for the diagnosed condition and whether the proposed charge is reasonable or unreasonable, based on at least the historical data, wherein the determining whether the proposed charge is reasonable or unreasonable includes comparing the proposed charge to a threshold value selected based on the historical data of past charges for the proposed medical service for determining that the proposed charge is presumptively unreasonable if the charge is above the threshold value, but reasonable if the proposed charge is at or below the threshold value;

providing feedback to the requesting device on whether the proposed medical service is medically necessary and reasonably charged prior to the rendering of the medical service by the medical provider, wherein if the proposed medical service is determined to be medically necessary and reasonably charged, the feedback includes pre-approval for the received medical claim for ensuring payment to the medical provider according to the proposed charge; and if the proposed medical service is determined to be medically unnecessary based on at least the historical data, prompting the medical provider to submit information justifying the proposed service for reevaluating the proposed medical service; and if the proposed charge is determined to be unreasonable based on at least the historical data, determining a reasonable amount that will be paid to the medical provider and informing the medical provider of the determined amount, the program instructions further including prompting the medical provider to submit information justifying the proposed charge for reevaluating the proposed charge.

35. The system of claim 34, wherein at least one of the one or more filters is a heat filter, and the program instructions for determining of whether the proposed medical service is medically necessary based on the heat filter include program instructions for:

identifying a date of injury;
identifying a timing of the proposed medical service, wherein the proposed medical service is a heat-based therapy; and
determining that the medical service is medically necessary based on the timing of the heat-based therapy relative to the date of injury.

36. The system of claim 34, wherein at least one of the one or more filters is a rarity filter, and the program instructions for determining whether the proposed medical service is medically necessary based on the rarity filter include program instructions for:

retrieving from the historical database the historical data of medical services historically provided for the diagnosed medical condition;
identifying a rate in which the proposed medical service was provided for the identified diagnosis based on the retrieved historical data;
identifying a threshold rate; and
determining that the proposed medical service is medically necessary based on a determination that the identified rate is equal or above the threshold rate.

37. The system of claim 34, wherein at least one of the one or more filters is a utilization filter, and the program instructions for determining whether the proposed medical service is medically necessary based on the utilization filter include program instructions for:

receiving information on one of a number of visits and duration of care requested for rendering the proposed medical service;
analyzing the historical data in the historical database on one of a number of visits and durations of care provided historically for the diagnosed condition;
identifying one of a threshold number of visits and durations of care based on the analyzed data;
determining that the medical service is medically necessary based on a determination that one of the requested number of visits and duration of care is equal or below the identified threshold number.

38. The system of claim 34, wherein at least one of the one or more filters is a level of service filter, and the program instructions for determining whether the proposed medical service is medically necessary based on the level of service filter include program instructions for:

identifying a level of service associated with the proposed medical service;
analyzing the historical data in the historical database on levels of service provided historically for the diagnosed condition;
identifying a threshold level of service based on the analyzed data; and
determining that the medical service is medically necessary based on a determination that the identified level of service is equal or below the threshold level of service.

39. The system of claim 34, wherein at least one of the one or more filters is a billing guidelines filter, and the program instructions for determining whether the proposed charge is reasonable or unreasonable based on the billing guidelines filter include program instructions for:

identifying a billing guideline associated with the proposed medical service; and
determining that the proposed charge is reasonable if the proposed charge complies with the identified billing guideline.

40. The system of claim 34, wherein at least one of the one or more filters is a charges filter, and the program instructions for determining whether the proposed charge is reasonable or unreasonable include program instructions for:

analyzing the historical data including total charges for the diagnosed condition;
identifying based on the analyzed historical data, a percentile distribution value for proposed total charges for the diagnosed condition; and
determining that the proposed total charges is reasonable if the percentile distribution value for the proposed total charges is equal or below a predetermined percentile distribution value.

41. The system of claim 34, wherein the feedback is a letter configured to be generated in real time with the determining of whether the proposed medical service is medically necessary.

42. The system of claim 34, wherein the program instructions for applying at least one of the one or more filters include program instructions for:

identifying the patient for whom the medical service is proposed;
retrieving historical data of medical care provided to the patient; and
determining based on the retrieved historical data for the patient that the proposed medical service is medically necessary for the patient if the proposed medical service is not inconsistent with prior medical services received by the patient.

43. The system of claim 34, wherein the threshold value for determining whether a proposed charge is reasonable or unreasonable for a first user differs from the threshold value for determining whether a proposed charge is reasonable or unreasonable for a second user.

44. The system of claim 34, wherein the threshold value is a threshold dollar amount.

45. The system of claim 44, wherein the threshold value is associated with a percentile distribution value indicating a percent of the past charges in the historical database at or below the threshold dollar amount.

46. The system of claim 45, wherein the percentile distribution value is selected by a user for determining whether the proposed charge is reasonable or unreasonable.

47. The system of claim 45, wherein the percentile distribution value is selected by the user from a plurality of possible percentile distribution values stored in the historical database.

48. The system of claim 45, wherein the selected percentile distribution value is 80%.

49. The system of claim 45, wherein the percentile distribution value selected by a first user differs from the percentile distribution value selected by a second user.

50. The system of claim 34, wherein the service code is a medical diagnosis code.

51. The system of claim 50, wherein the service code is an international classification of diseases code.

52. The system of claim 34, wherein the one or more filters are medical procedure filters.

53. The system of claim 34, wherein the one or more filters are configured to implement rules provided by one or more medical organizations.

54. The system of claim 34, wherein the one or more filters are associated with specific geographic locations.

55. The system of claim 34, wherein the one or more filters are configured to apply a first set of rules based on a first type of medical claim, and a second set of rules based on a second type of medical claim.

56. A computerized medical care system for providing pre-approval for medical services and charges associated with the medical services, the system comprising:
   a computing engine configured to receive over a data communications network a medical claim including a diagnosis code identifying diagnosis of a medical condition for a patient, a service code identifying a proposed medical service, and a proposed charge for the medical service;
   a data storage device storing a historical database of patient records with historical data on medical procedures rendered to at least a plurality of other patients for the diagnosed condition, wherein the historical data includes data of past charges for the proposed medical service; and
   a plurality of medical procedure filters coupled to the engine and configured to determine whether the proposed medical service is medically necessary relative to the diagnosis and whether the proposed charge is reasonable or unreasonable, based on at least the historical data, wherein the determining whether the proposed charge is reasonable or unreasonable includes comparing the proposed charge to a threshold value selected based on the historical data of past charges for the proposed medical service for determining that the proposed charge is presumptively unreasonable if the charge is above the threshold value, but reasonable if the proposed charge is at or below the threshold value,
   wherein the computing engine is configured to provide feedback over the data communications network on whether the proposed medical service is medically necessary and reasonably charged based on at least the historical data on the medical procedures rendered to at least the plurality of other patients for the diagnosed condition, prior to rendering of the medical service by a medical provider, wherein if the proposed medical service is determined to be medically unnecessary based on at least the historical data, the computing engine is further configured to prompt the medical provider to submit information justifying the proposed service for reevaluating the proposed medical service, and if the proposed charge is determined to be unreasonable based on at least the historical data, the computing engine is configured to determine a reasonable amount that will be paid to the medical provider and inform the medical provider of the determined amount, the computing engine being further configured to prompt the medical provider to submit information justifying the proposed charge for reevaluating the proposed charge.

57. The system of claim 56, wherein at least one of the plurality of filters is a heat filter and the computing engine is configured to determine whether the proposed medical service is medically necessary based on the heat filter, the determining including:
   identifying a date of injury;
   identifying a timing of the proposed medical service, wherein the proposed medical service is a heat-based therapy; and
   determining that the medical service is medically necessary based on the timing of the heat-based therapy relative to the date of injury.

58. The system of claim 56, wherein at least one of the one or more filters is a rarity filter and the computing engine is configured to determine whether the proposed medical service is medically necessary based on the rarity filter, the determining including:
   retrieving from the historical database the historical data of medical services historically provided for the diagnosed medical condition;
   identifying a rate in which the proposed medical service was provided for the identified diagnosis based on the retrieved historical data;
   identifying a threshold rate; and
   determining that the proposed medical service is medically necessary based on a determination that the identified rate is equal or above the threshold rate.

59. The system of claim 56, wherein at least one of the one or more filters is a utilization filter and the computing engine is configured to determine whether the proposed medical service is medically necessary based on the utilization filter, the determining including:
   receiving information on one of a number of visits and duration of care requested for rendering the proposed medical service;
   analyzing the historical data in the historical database on one of a number of visits and durations of care provided historically for the diagnosed condition;
   identifying one of a threshold number of visits and durations of care based on the analyzed data;
   determining that the medical service is medically necessary based on a determination that one of the requested number of visits and duration of care is equal or below the identified threshold number.

60. The system of claim 56, wherein at least one of the one or more filters is a level of service filter and the computing engine is configured to determine whether the proposed medical service is medically necessary based on the level of service filter, the determining including:
   identifying a level of service associated with the proposed medical service;
   analyzing the historical data in the historical database on levels of service provided historically for the diagnosed condition;
   identifying a threshold level of service based on the analyzed data; and
   determining that the medical service is medically necessary based on a determination that the identified level of service is equal or below the threshold level of service.

61. The system of claim 56, wherein at least one of the one or more filters is a billing guidelines filter and the computing engine is configured to determine whether the proposed charge is reasonable or unreasonable based on the billing guidelines filter, the determining including:
   identifying a billing guideline associated with the proposed medical service; and
   determining that the proposed charge is reasonable if the proposed charge complies with the identified billing guideline.

62. The system of claim 56, wherein at least one of the one or more filters is a charges filter and the computing engine is configured to:
   analyze the historical data including total charges for the diagnosed condition;
   identify based on the analyzed historical data, a percentile distribution value for proposed total charges for the diagnosed condition; and
   determine that the proposed total charges is reasonable if the percentile distribution value for the proposed total charges is equal or below a predetermined percentile distribution value.

63. The system of claim 56, wherein the feedback is a letter configured to be generated in real time with the determining of whether the proposed medical service is medically necessary.

64. The system of claim 56, wherein the computing engine is further configured to:
- identify the patient for whom the medical service is proposed;
- retrieve historical data of medical care provided to the patient; and
- determine based on the retrieved historical data for the patient that the proposed medical service is medically necessary for the patient if the proposed medical service is not inconsistent with prior medical services received by the patient.

65. The system of claim 56, wherein the threshold value for determining whether a proposed charge is reasonable or unreasonable for a first user differs from the threshold value for determining whether a proposed charge is reasonable or unreasonable for a second user.

66. The system of claim 56, wherein the threshold value is a threshold dollar amount.

67. The system of claim 66, wherein the threshold value is associated with a percentile distribution value indicating a percent of the past charges in the historical database at or below the threshold dollar amount.

68. The system of claim 67, wherein the percentile distribution value is configured to be selected by a user for determining whether the proposed charge is reasonable or unreasonable.

69. The system of claim 68, wherein the percentile distribution value is configured to be selected by the user from a plurality of possible percentile distribution values stored in the historical database.

70. The system of claim 67, wherein the selected percentile distribution value is 80%.

71. The system of claim 67, wherein the percentile distribution value selected by a first user differs from the percentile distribution value selected by a second user.

72. The system of claim 56, wherein the service code is a medical diagnosis code.

73. The system of claim 72, wherein the service code is an international classification of diseases code.

74. The system of claim 56, wherein the one or more filters are medical procedure filters.

75. The system of claim 56, wherein the one or more filters are configured to implement rules provided by one or more medical organizations.

76. The system of claim 56, wherein the one or more filters are associated with specific geographic locations.

77. The system of claim 56, wherein the one or more filters are configured to apply a first set of rules based on a first type of medical claim, and a second set of rules based on a second type of medical claim.

* * * * *